United States Patent [19]
Sprecker et al.
[11] Patent Number: 4,772,583
[45] Date of Patent: Sep. 20, 1988

[54] BETA-ALKYLIDENE PHENETHYL ALCOHOL ESTERS AND ETHERS, ORGANOLEPTIC USES THEREOF AND PROCESSES FOR PREPARING SAME

[75] Inventors: Mark A. Sprecker, Sea Bright; Robert P. Belko, Woodbridge; Richard M. Boden, Ocean; Marie R. Hanna, Hazlet, all of N.J.

[73] Assignee: International Flavors & Fragrances Inc., New York, N.Y.

[21] Appl. No.: 134,817

[22] Filed: Dec. 18, 1987

Related U.S. Application Data

[63] Continuation-in-part of Ser. No. 92,756, Sep. 3, 1987.

[51] Int. Cl.[4] .......... A61K 7/46
[52] U.S. Cl. .......... 512/12; 512/21; 512/4; 558/275; 558/291; 568/627; 252/174.11
[58] Field of Search .......... 512/12, 21; 558/275, 558/291; 568/627; 252/174.11

[56] References Cited

U.S. PATENT DOCUMENTS 3,189,638 6/1965 Bengelsdorf .......... 558/291
3,239,421 3/1966 Bengelsdorf .......... 558/291

FOREIGN PATENT DOCUMENTS 3007232 9/1981 Fed. Rep. of Germany .......... 512/21

*Primary Examiner*—James H. Reamer
*Attorney, Agent, or Firm*—Arthur L. Liberman

[57] ABSTRACT

Described is the novel compound genus the beta-alkylidene phenethyl alcohol esters and ethers of our invention defined according to the generic structure:

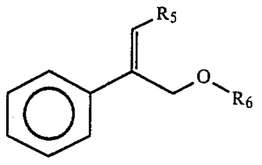

wherein $R_5$ represents hydrogen or methyl; wherein $R_6$ represents one of the moieties:

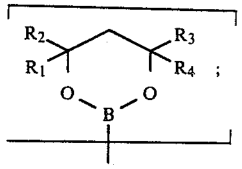

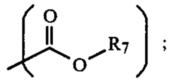

or

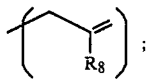

wherein $R_1$, $R_2$, $R_3$ and $R_4$ each represents the same or different hydrogen or methyl; wherein $R_7$ represents methyl or ethyl; and wherein $R_8$ represents hydrogen or methyl; useful in augmenting or enhancing the aroma of consumable materials including perfumes, colognes and perfumed articles including solid or liquid anionic, cationic, nonionic or zwitterionic detergents, fabric softener articles, fabric softener compositions, cosmetic powders and hair preparations.

7 Claims, 17 Drawing Sheets

GLC PROFILE FOR EXAMPLE I(A).

NMR SPECTRUM FOR EXAMPLE I(A).

GLC PROFILE FOR EXAMPLE I(A).

NMR SPECTRUM
FOR EXAMPLE I(A).

GLC PROFILE FOR EXAMPLE I(B).

NMR SPECTRUM FOR EXAMPLE I(B).

GLC PROFILE FOR EXAMPLE II.

NMR SPECTRUM FOR EXAMPLE I.

GLC PROFILE FOR EXAMPLE III.

NMR SPECTRUM FOR EXAMPLE III.

GLC PROFILE FOR EXAMPLE IV.

NMR SPECTRUM FOR EXAMPLE IV.

GLC PROFILE FOR EXAMPLE V.
CRUDE

GLC PROFILE FOR EXAMPLE V
BULKED FRACTIONS
4-8

NMR SPECTRUM FOR EXAMPLE V.

IR SPECTRUM FOR EXAMPLE V.

BETA-ALKYLIDENE PHENETHYL ALCOHOL ESTERS AND ETHERS, ORGANOLEPTIC USES THEREOF AND PROCESSES FOR PREPARING SAME

This application is a continuation-in-part of application for U.S. Pat. Ser. No. 092,756 filed on Sept. 3, 1987.

BACKGROUND OF THE INVENTION

This invention relates to beta-alkylidene phenethyl alcohol esters and ethers of our invention defined according to the generic structure:

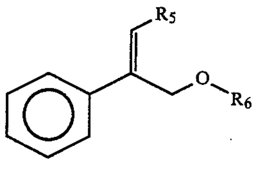

wherein $R_5$ represents hydrogen or methyl; wherein $R_6$ represents one of the moieties:

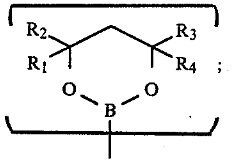

;

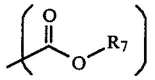

;

or

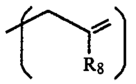

;

wherein $R_1$, $R_2$, $R_3$ and $R_4$ each represents the same or different hydrogen or methyl; wherein $R_7$ represents methyl or ethyl; and wherein $R_8$ represents hydrogen or methyl; and uses thereof in augmenting or enhancing the aroma of perfume compositions or perfumed articles including perfumed polymers.

Materials which can provide rose, cinnamon, carnation, lilac, spicy, ozoney and green aromas with spicy, clove, lilac, piney, anisic and fruity topnotes particularly those materials which are relatively inexpensive are highly sought after in the art of perfumery. Many of the natural materials which provide such fragrance profiles and contribute such desired nuances to perfumery compositions and perfumed articles are high in cost, vary in quality from one batch to another and/or are generally subject to the usual variations of natural products.

There is, accordingly, a continuing effort to find synthetic materials which will replace the essential fragrance notes produced by natural essential oils or compositions thereof. Unfortunately, many of these synthetic materials either have the desired nuances only to a relatively small degree or else contribute undesirable or unwanted odor to the composition. The search for more materials which can provide a more refined rose, cinnamon, carnation, lilac, spicy, ozoney and green aroma profile and spicy, clove, lilac, piney, anisic and fruity topnotes has been difficult and relatively costly in the area of both natural products and synthetic products.

Aryl alkanols are known as perfumery materials particularly the well known phenylethyl alcohol which provides rose, cinnamon and honey aromas to floral fragrance formulations and perfumed articles.

Beta-methylene phenethyl acetate having the structure:

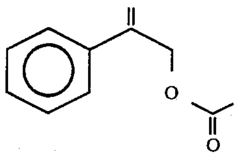

is disclosed to provide sweet, lilac, hyacinth and ripe grain aromas to perfumed articles and perfume formulations in Canadian Letters Pat. No. 1,157,036 issued on Nov. 15, 1983 as well as European Pat. No. 035,183 published on Feb. 20, 1981. The said European and Canadian Patents also disclose other esters of methylene phenethyl alcohol useful in perfumery but do not disclose carbonate esters, ethers or borate esters and furthermore do not disclose the alcohol itself to be so useful.

Indeed, the alkylidene phenethyl alcohols of our invention have unexpected, unobvious and advantageous intense aromas and give rise to unexpected, unobvious and advantageous properties with respect to perfume compositions, perfumed articles and perfumed polymers.

The use of the borate esters in perfumery is indeed disclosed in U.S. Pat. No. 3,239,421 issued on Mar. 8, 1966 (entitled "Perfume Composition Containing 2-(beta-phenylethoxy)-4,4,6-trimethyl-1,3-dioxa-2-borinane) the specification for which is incorporated by reference herein.

Furthermore, the use of boric acid esters as intermediates in the synthesis of chemicals useful in augmenting or enhancing the aroma of perfumes and perfume compositions is also disclosed in the prior art.

Thus, the borate ester of 3-endo-methyl-3-exo(4'-methyl-5'-hydroxypentyl)norcamphor is shown as an intermediate for producing dihydro-beta-santalol in U.S. Pat. No. 3,662,007 issued on May 9, 1972.

However, arylalkanol esters of boric acid and glycol borates are shown to be useful for killing bacteria and fungi in U.S. Pat. No. 3,564,091 issued on Feb. 16, 1971. Indeed, the compound having the structure:

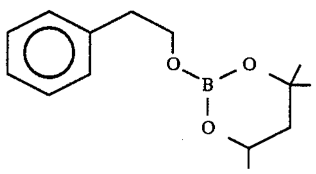

is shown to be useful in said U.S. Pat. No. 3,564,091 issued on Feb. 16, 1971 and the preparation of this compound is set forth at column 4, lines 35–48 of U.S. Pat.

No. 3,564,091 the specification for which is incorporated by reference herein.

This compound is also shown to be useful in the perfumery art in copending application for U.S. Pat. Ser. No. 073,289 filed on July 14, 1987 the specification for which is incorporated by reference herein.

The use as a precursor of the genus defined according to the structure:

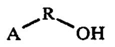

wherein A is an aryl hydrocarbon group of 5-14 carbon atoms and R is an aliphatic hydrocarbon group of more than one carbon atom and the compound:

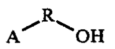

may be phenylethyl alcohol is set forth at lines 40-52, at column 1 of U.S. Pat. No. 3,564,091, to wit:

> "More particularly, this invention relates to the use of biocides, compounds selected from the group consisting of (1) esters of boric acid and an alcohol of the formula A—R—OH, wherein A is an aryl hydrocarbon group of 5-14 carbon atoms and R is an aliphatic hydrocarbon group of more than one carbon atom, and (2) A—R—OH alcohol esters of glycol orthoborates wherein A and R are as described above.
>
> In the general formula above, A is preferably selected from the group consisting of phenyl, naphthyl, phenanthracyl, and anthracyl. The glycol is selected from the group consisting of alpha and beta glycols containing 3-20 carbon atoms. The term boric acid embraces ortho-, meta-, and pyroboric acids, and boric oxide."

U.S. Pat. No. 2,839,564 issued on June 17, 1958; U.S. Pat. No. 2,940,839 issued on June 14, 1960; and U.S. Pat. No. 3,189,637 issued on June 15, 1965 as well as United Kingdom Patent Specification No. 722,538 published on Jan. 26, 1955 each disclose borate esters having the generic structure:

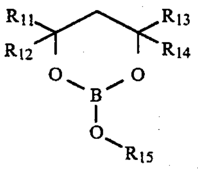

wherein $R_{11}$, $R_{12}$, $R_{13}$ and $R_{14}$ can represent hydrogen or alkyl and $R_{15}$ represent various hydrocarbon moieties (for example the definition of the R moieties at column 1, lines 29-34 of U.S. Pat. No. 2,839,564 states:

> "wherein each R represents the same or different member of the group consisting of hydrogen and monovalent hydrocarbon radicals including alkyl, cycloalkyl, aryl, aralkyl and alkaryl groups, and R' represents a monovalent hydrocarbon radical including alkyl, cycloalkyl, aryl, aralkyl and alkaryl groups").

The borate esters having the generic structure:

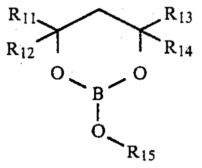

as disclosed in the aforementioned Patents and U.K. Patent Specificaton are indicated to be useful in causing fuel to be made more efficient on operation of internal combustion engines by reduction of octane requirements.

The prior art does not set forth explicitedly or implicitedly the use of such a genus or members of such a genus in perfumery or in perfumed articles or perfumed polymers.

U.S. Pat. No. 4,391,999 issued on July 5, 1983 entitled:

> "3,4,5,6,6-PENTAMETHYL HEXANOL-2-AND ALKYL HOMOLOGUES THEREOF; PROCESS FOR PREPARING SAME AND ORGANOLEPTIC USES THEREOF"

on which I am the inventor, discloses the compound having the structure:

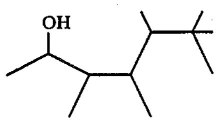

as being useful in augmenting or enhancing the aroma of perfume compositions and perfumed articles.

The publication "Perfume and Flavor Chemicals (Aroma Chemicals)", Volume I, by Steffen Arctander (1969) discloses the usefulness of the compounds having the structure:

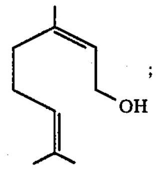 ; 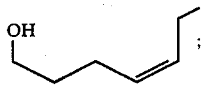 ;

and

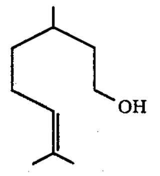

in augmenting or enhancing the aroma of perfume compositions at, inter alia, Monographs 1427 and 669.

Nothing in the prior art discloses the beta-alkylidene phenethyl alcohol esters and ethers of our invention defined according to the generic structure:

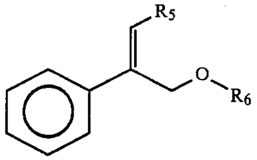

wherein $R_5$ represents hydrogen or methyl; wherein $R_6$ represents one of the moieties:

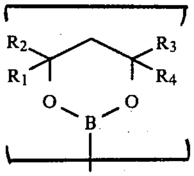

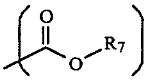

or

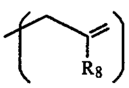

wherein $R_1$, $R_2$, $R_3$ and $R_4$ each represents the same or different hydrogen or methyl; wherein $R_7$ represents methyl or ethyl; and wherein $R_8$ represents hydrogen or methyl particularly as being useful in augmenting or enhancing the aroma of perfume compositions, perfumed articles and perfumed polymers.

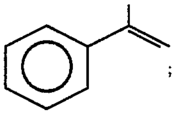 ; 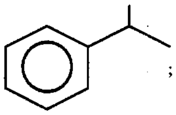 ;

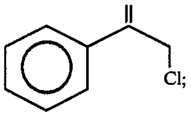 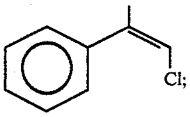

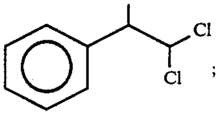 ;

and $CHCl_3$.

Figure 2:
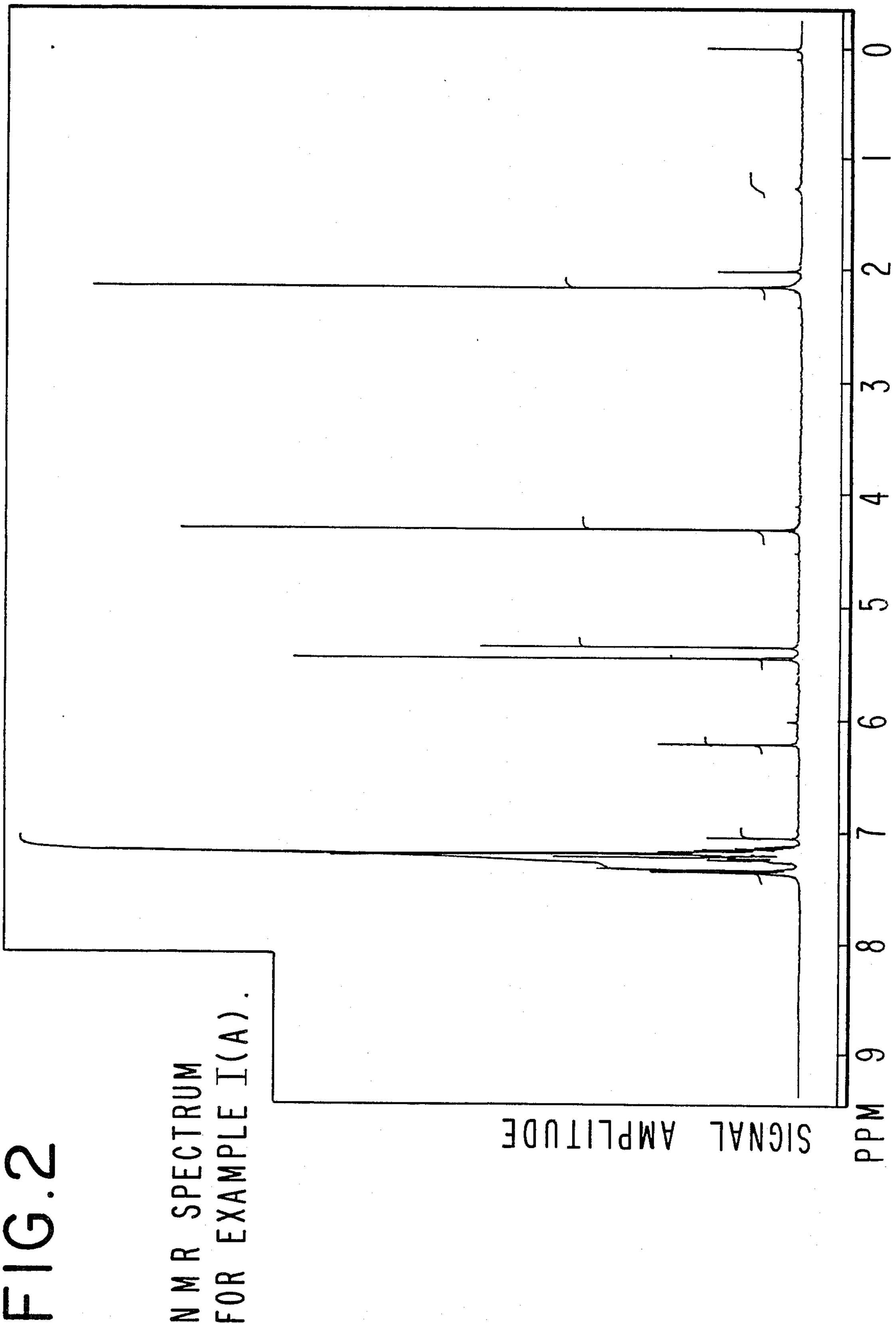

FIG. 2 is the NMR spectrum for the distillation product of the reaction product of Example I(A) containing the compounds having the structures:

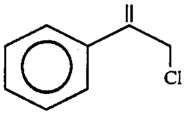 and 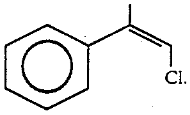

Figure 3:
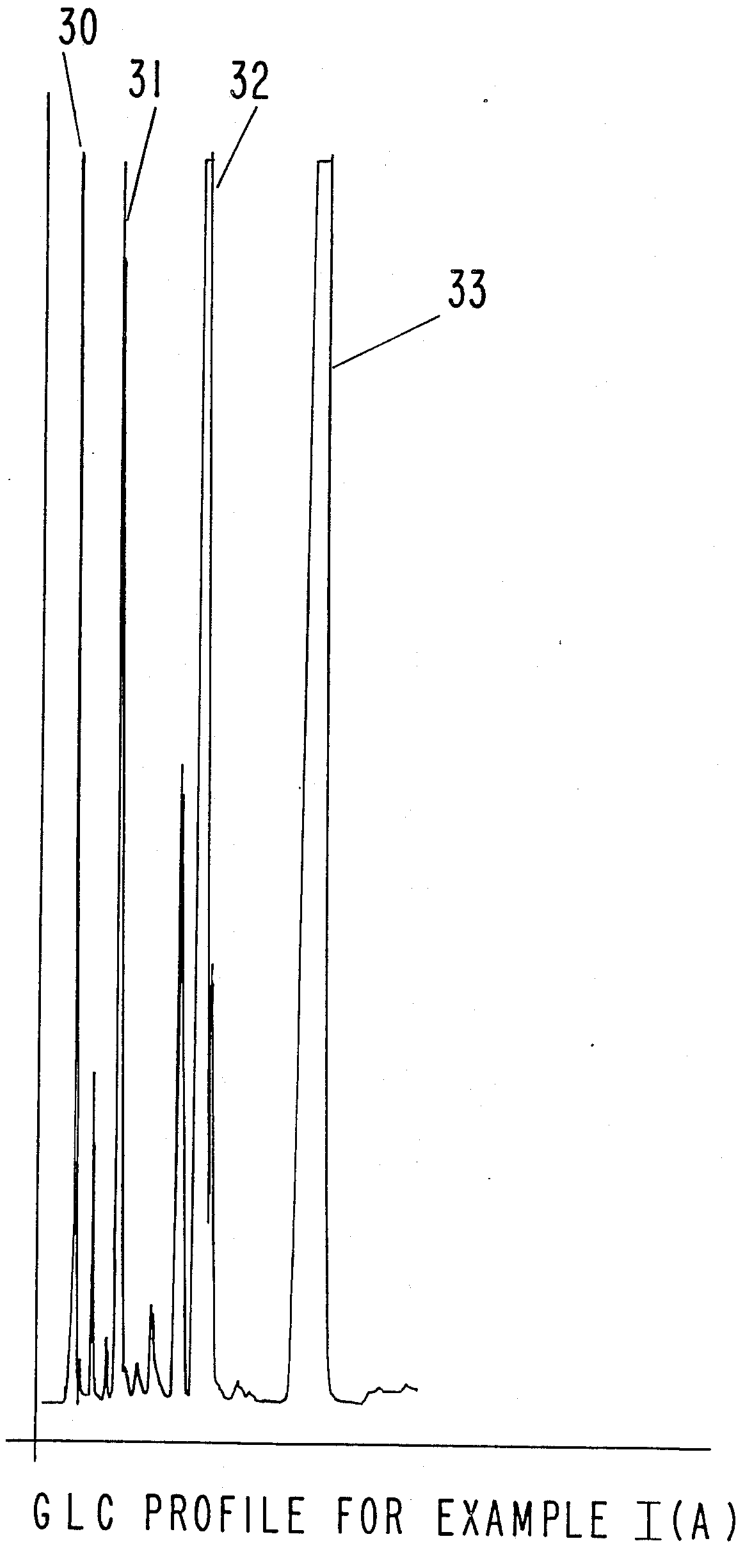

FIG. 3 is the GLC profile for the second step (second reaction) of Example I containing the compounds having the structures:

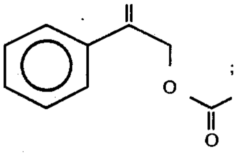 ; 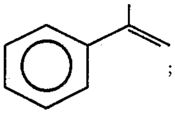 ;

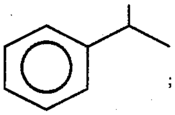 ; 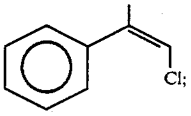

and $CHCl_3$.

Figure 4:
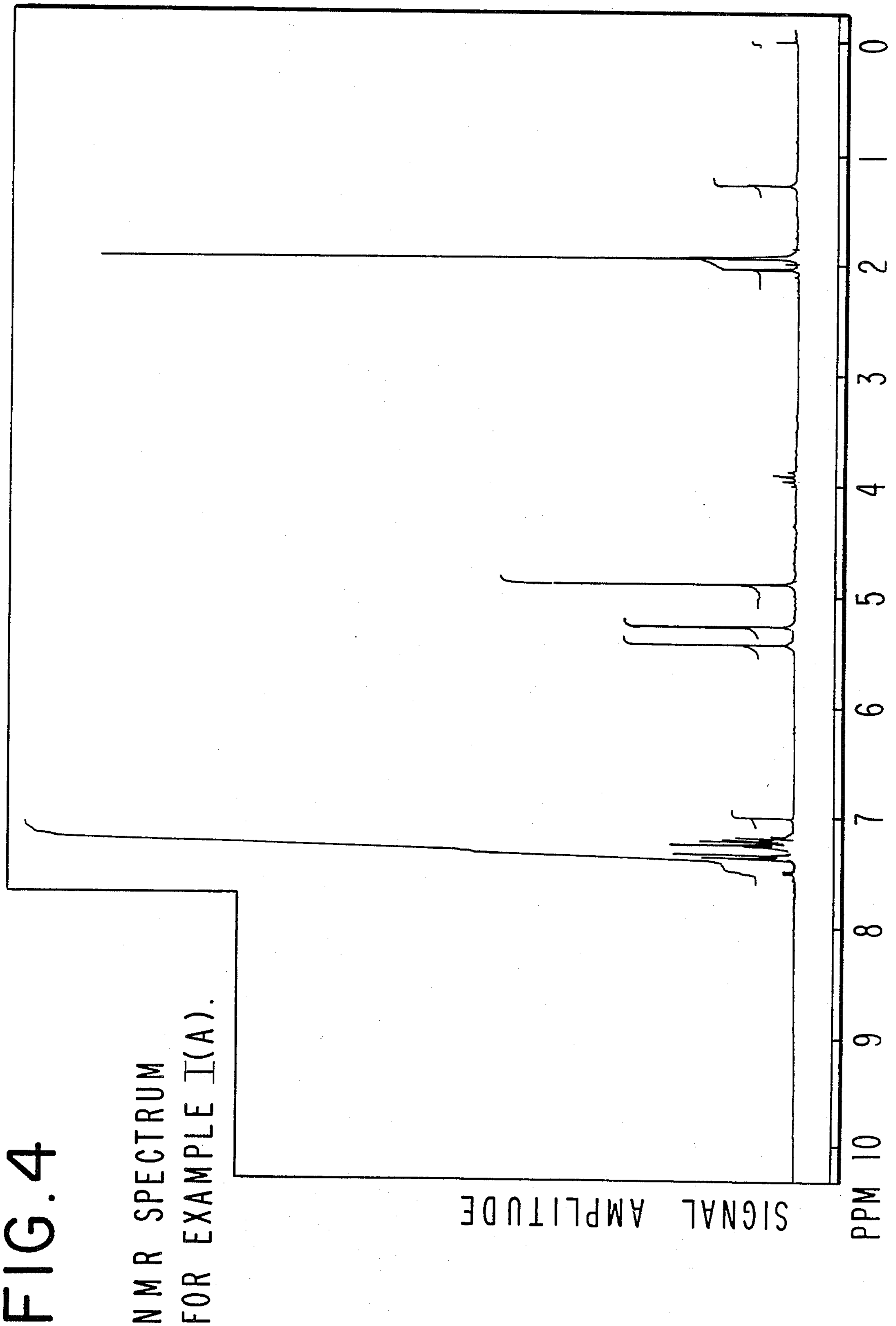

FIG. 4 is the NMR spectrum for the compound having the structure:

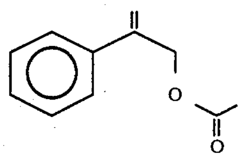

produced according to the second step of Example I(A).

Figure 5:
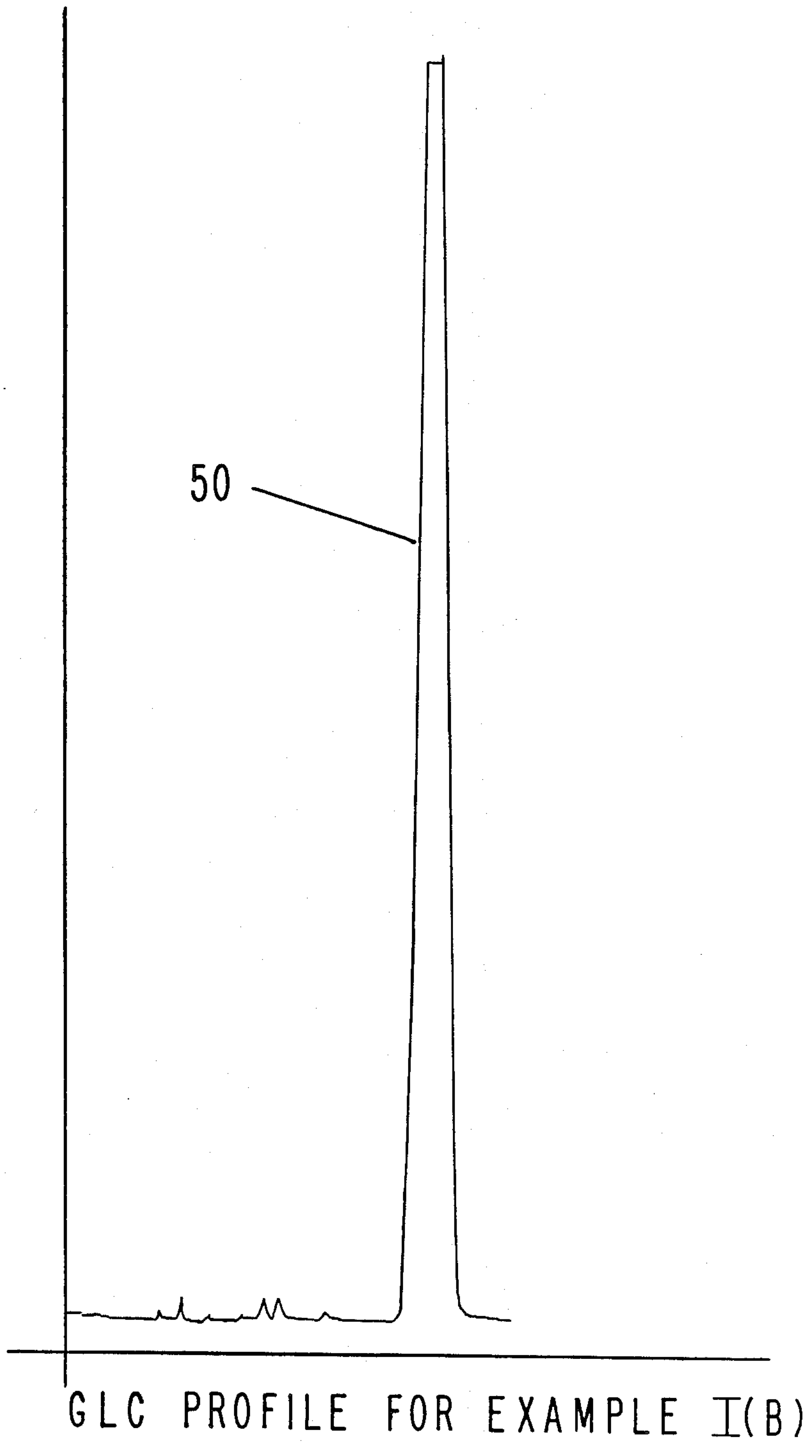

FIG. 5 is the GLC profile for the reaction product of Example I(B) containing the compound having the structure:

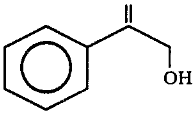

(Conditions: SE-30 column programmed at 180° C. isothermal).

Figure 6:
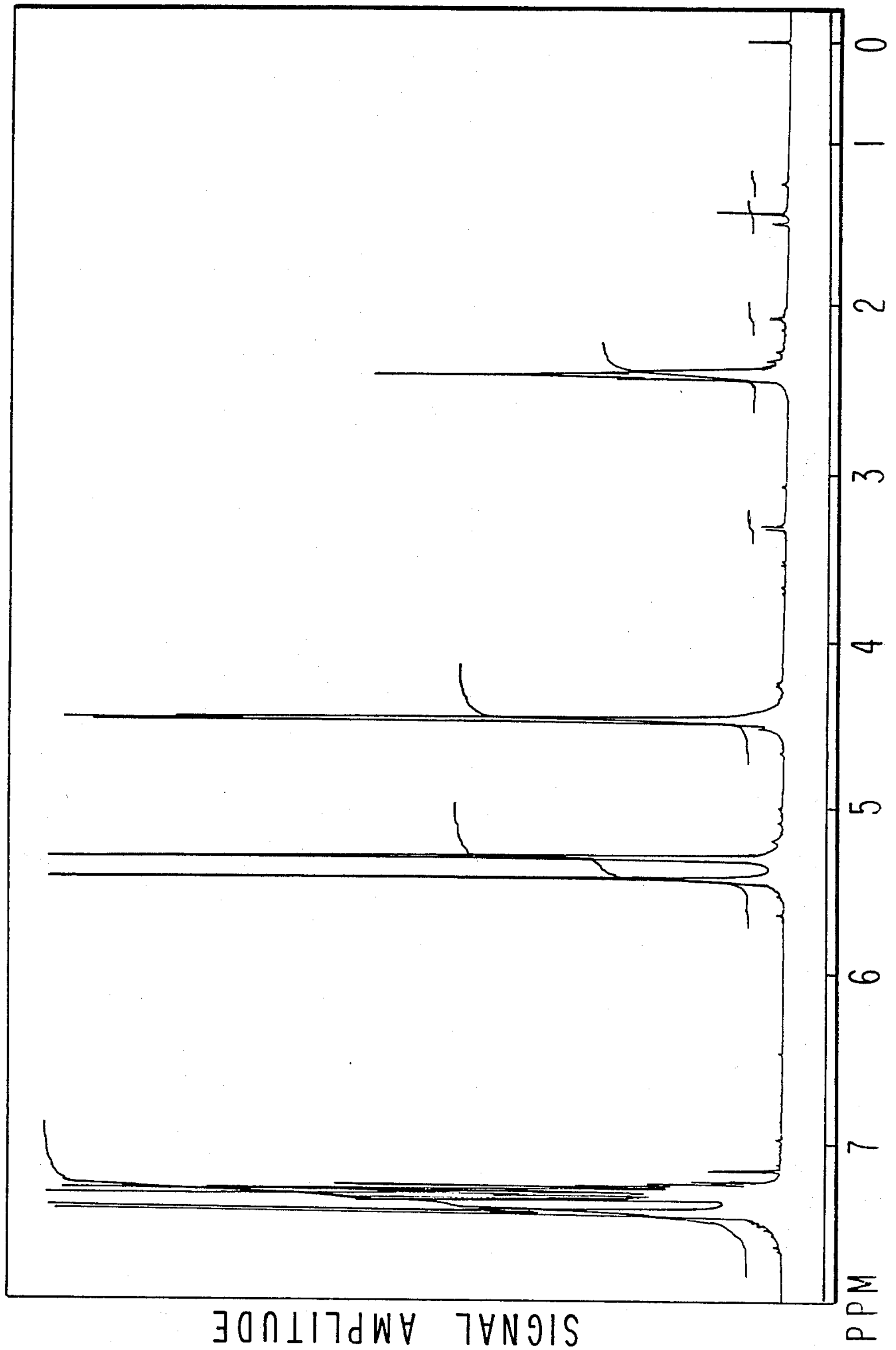

FIG. 6 is the NMR spectrum for the compound having the structure:

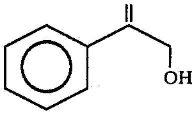

produced according to Example I(B).

Figure 7:
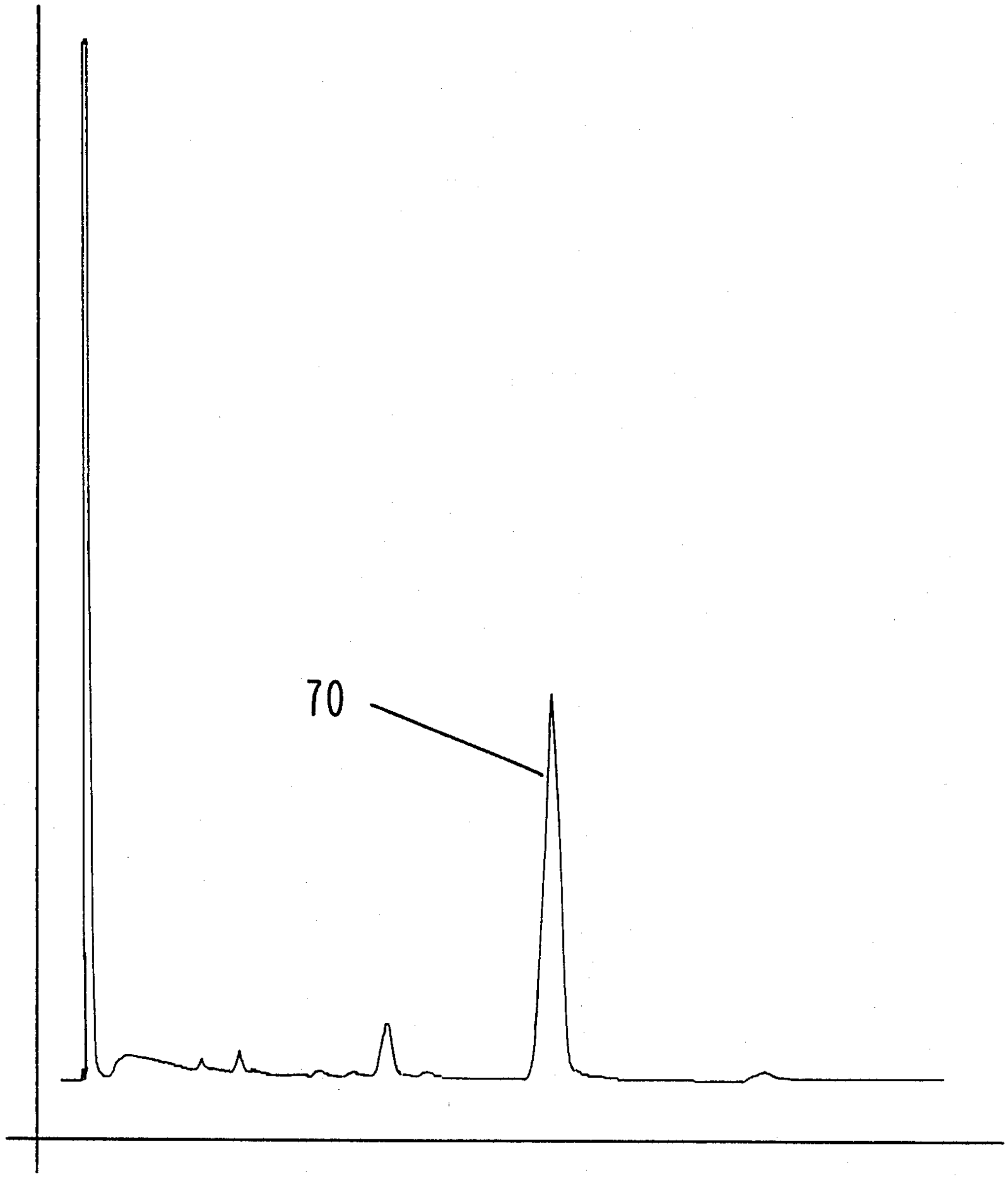

FIG. 7 is the GLC profile for the reaction product of Example II containing the compound having the structure:

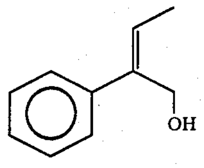

(Conditions: Carbowax column programmed at 180° C. isothermal).

Figure 8:
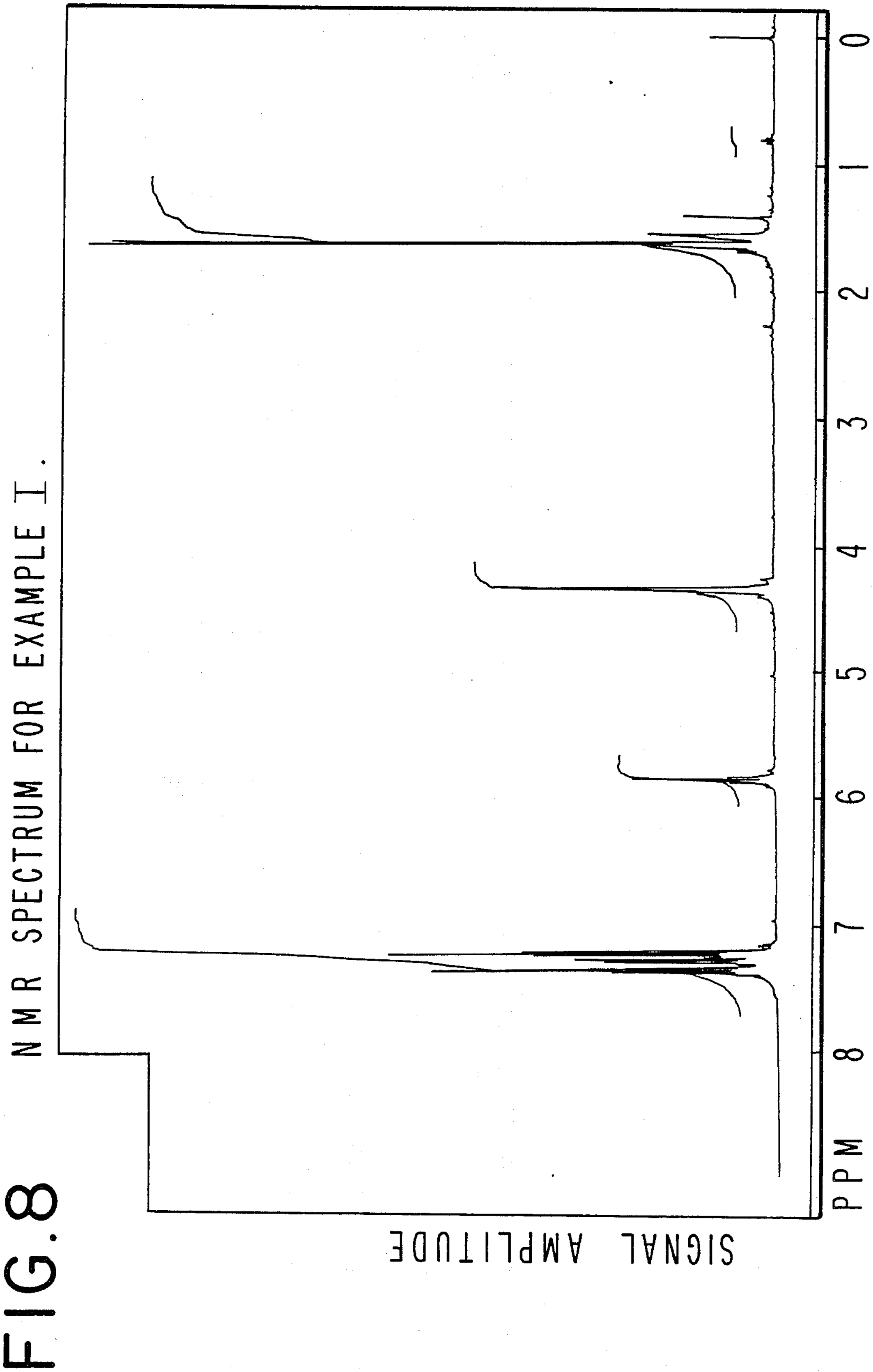

FIG. 8 is the NMR spectrum for the compound having the structure:

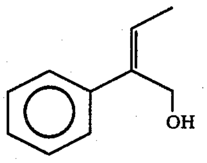

produced according to Example II.

Figure 9:
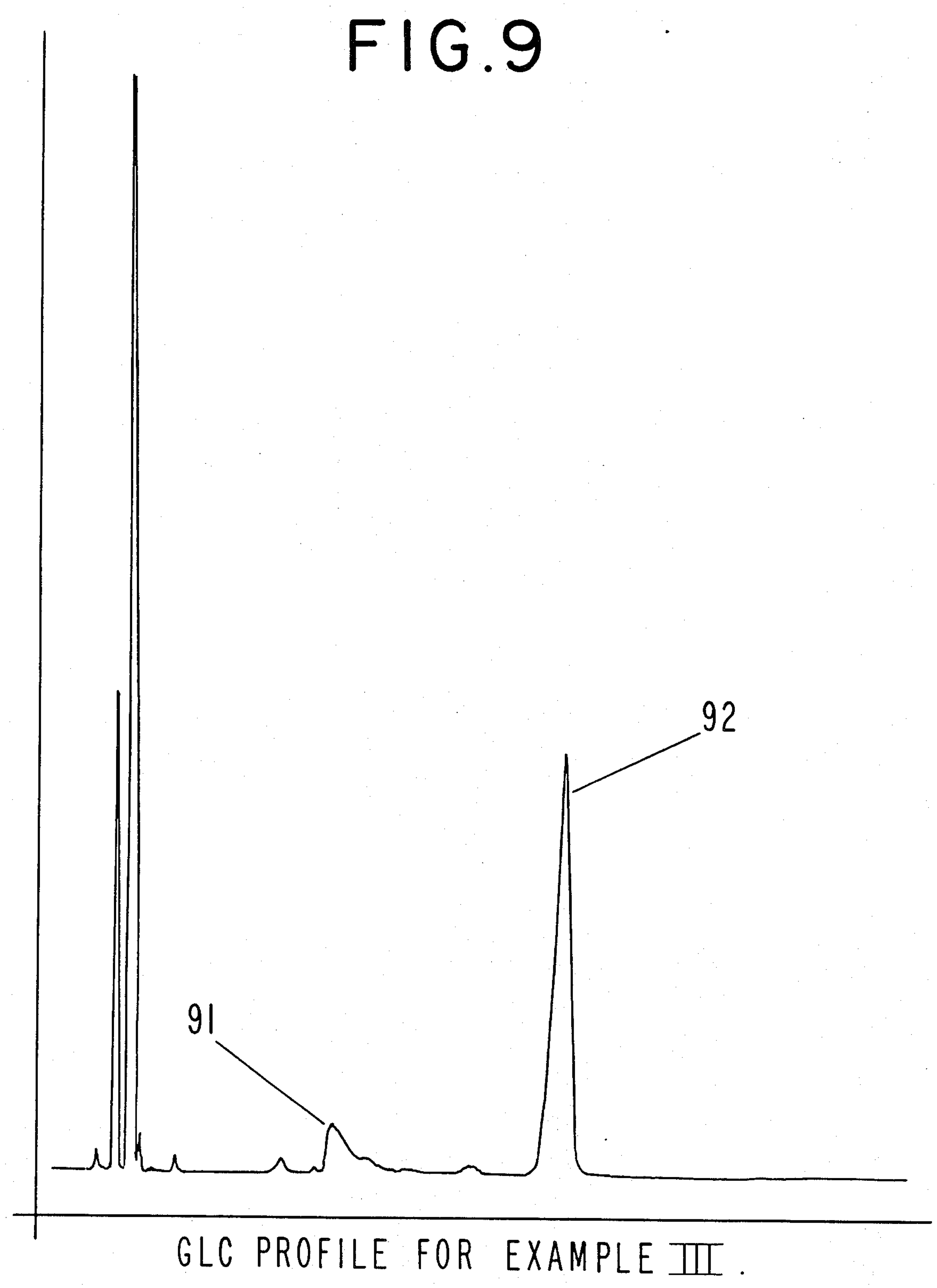

FIG. 9 is the GLC profile for the crude reaction product of Example III containing the compounds having the structures:

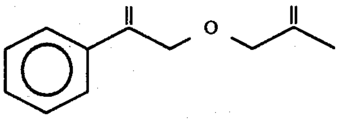

and

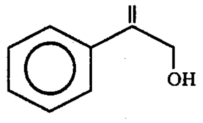

(Conditions: SE-30 column programmed at 180° C. isothermal).

Figure 10:
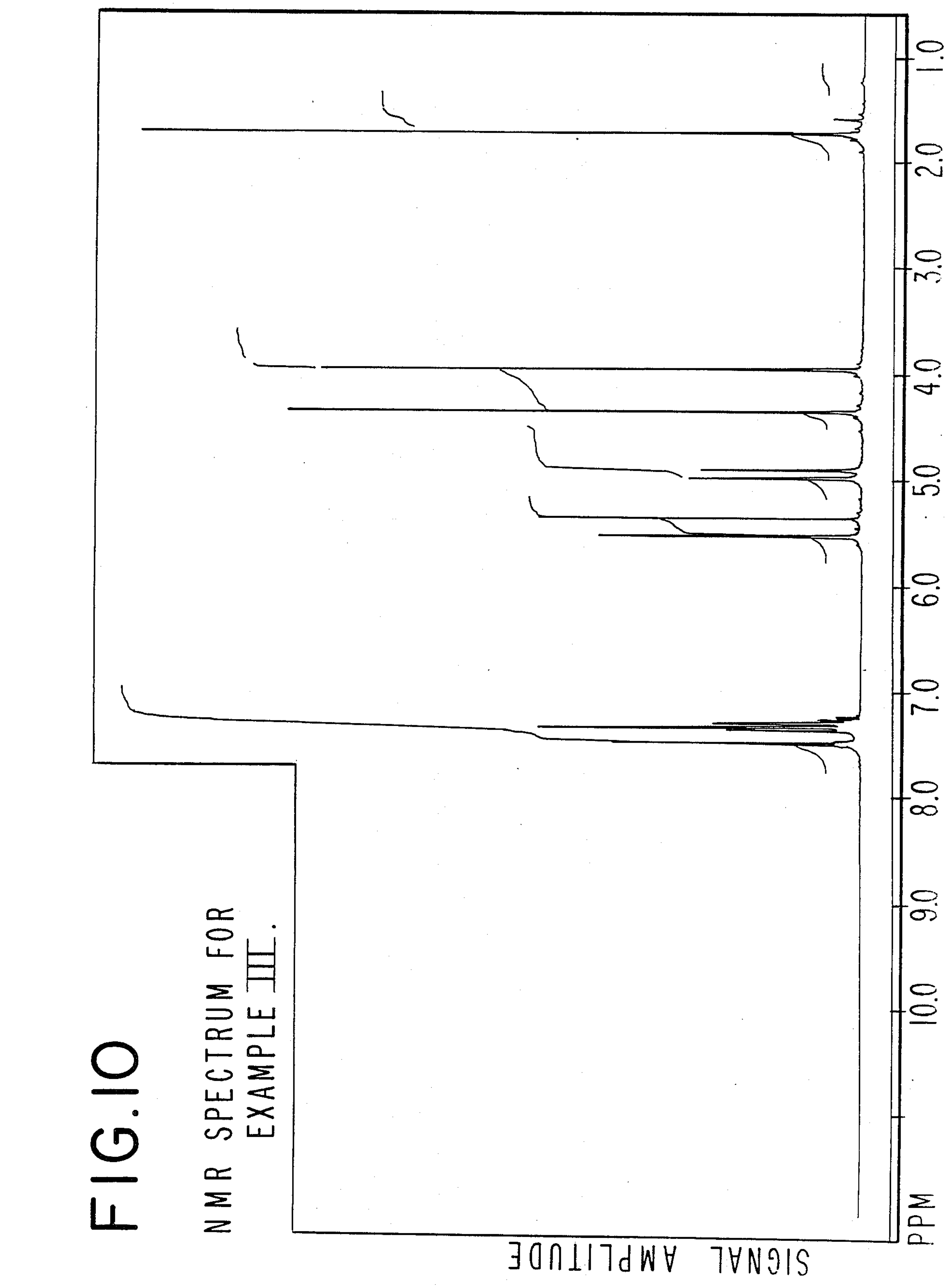

FIG. 10 is the NMR spectrum for the compound having the structure:

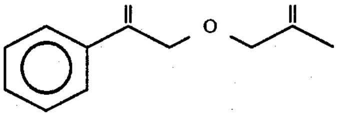

prepared according to Example III.

Figure 11:
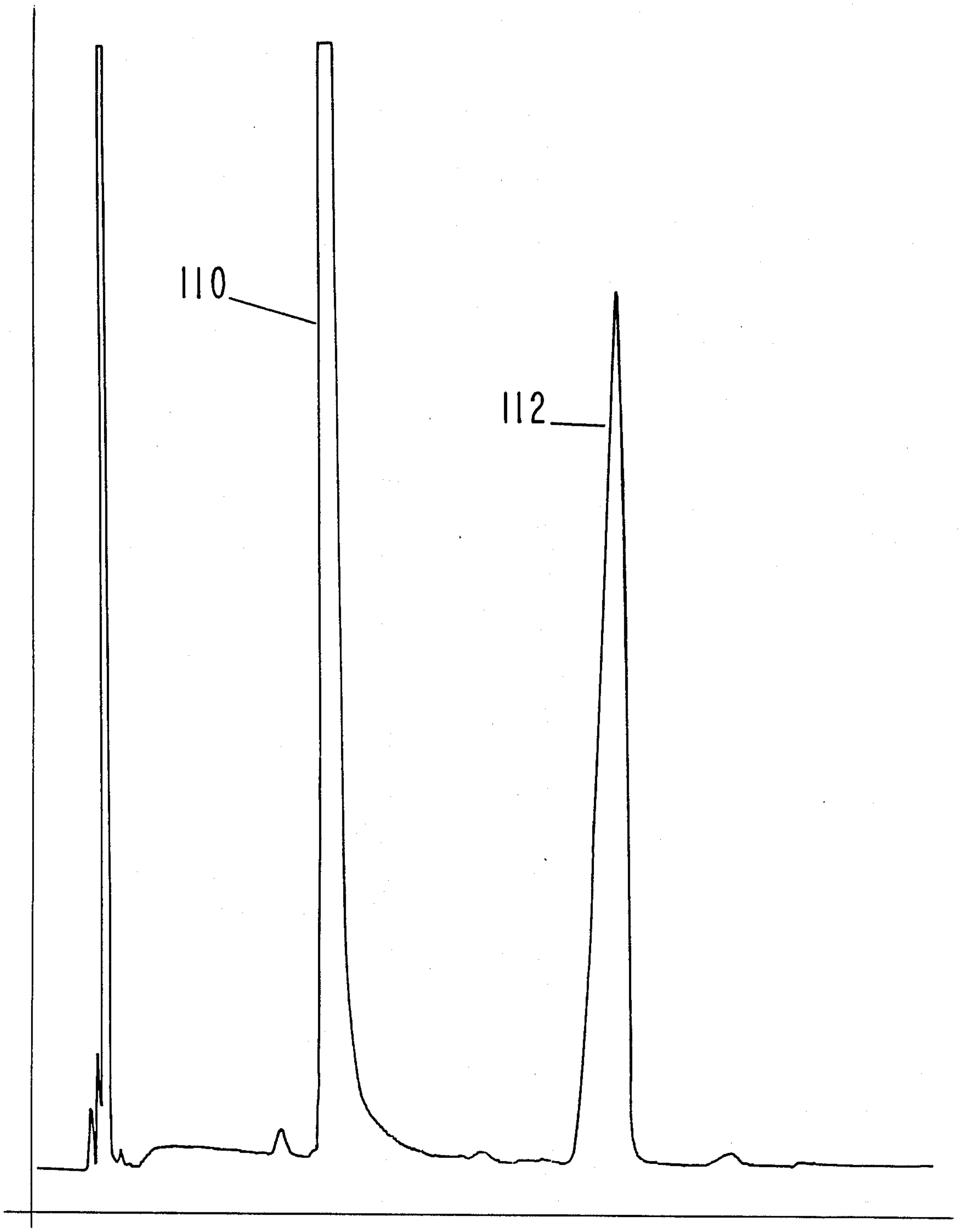

FIG. 11 is the GLC profile for the crude reaction product of Example IV containing the compounds having the structures:

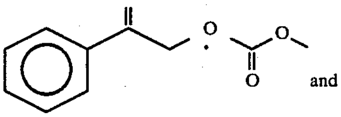

and

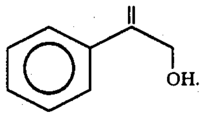

Figure 12:
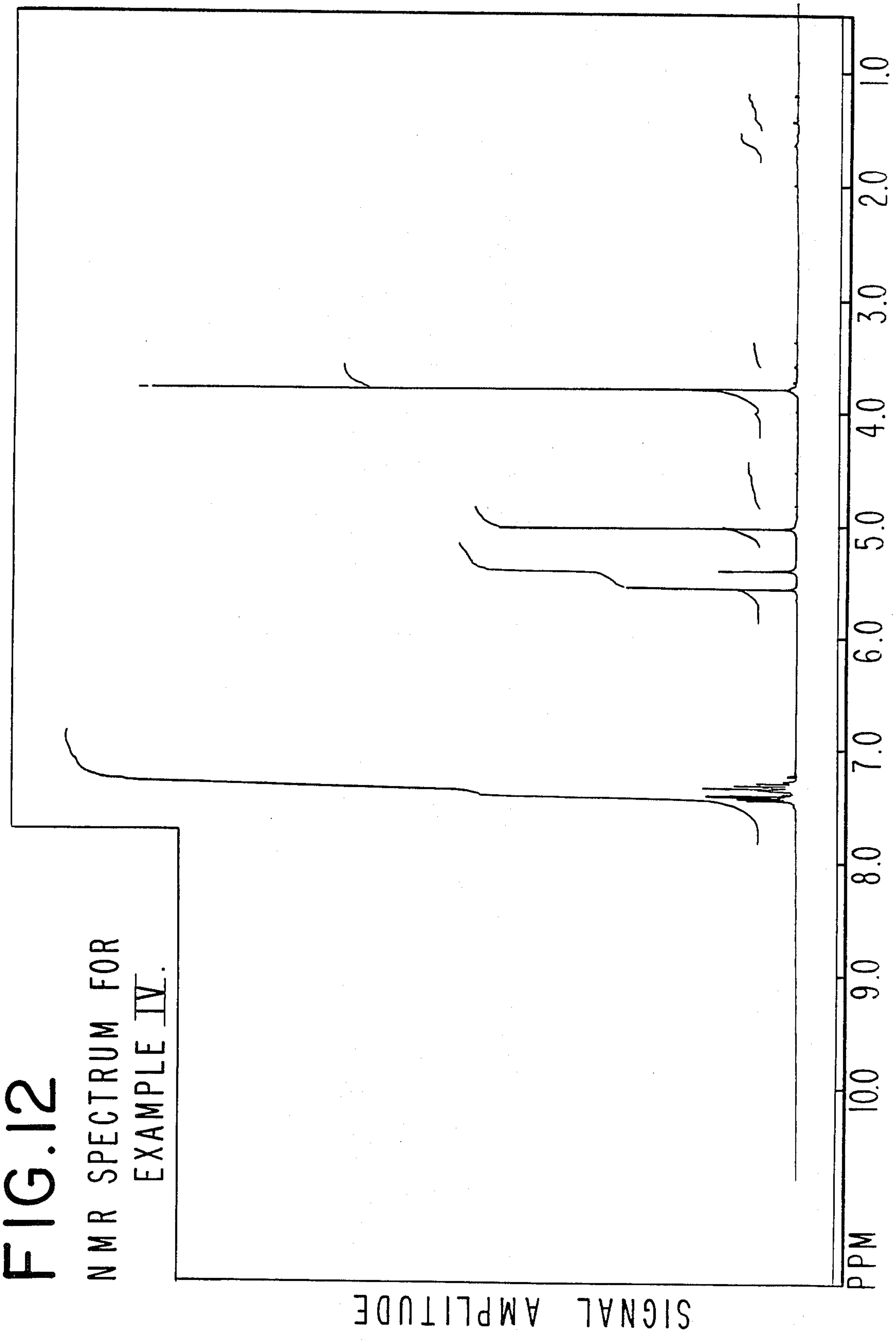

FIG. 12 is the NMR spectrum for the compound having the structure:

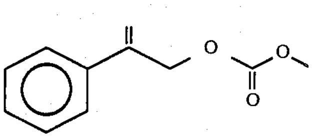

prepared according to Example IV.

Figure 13:
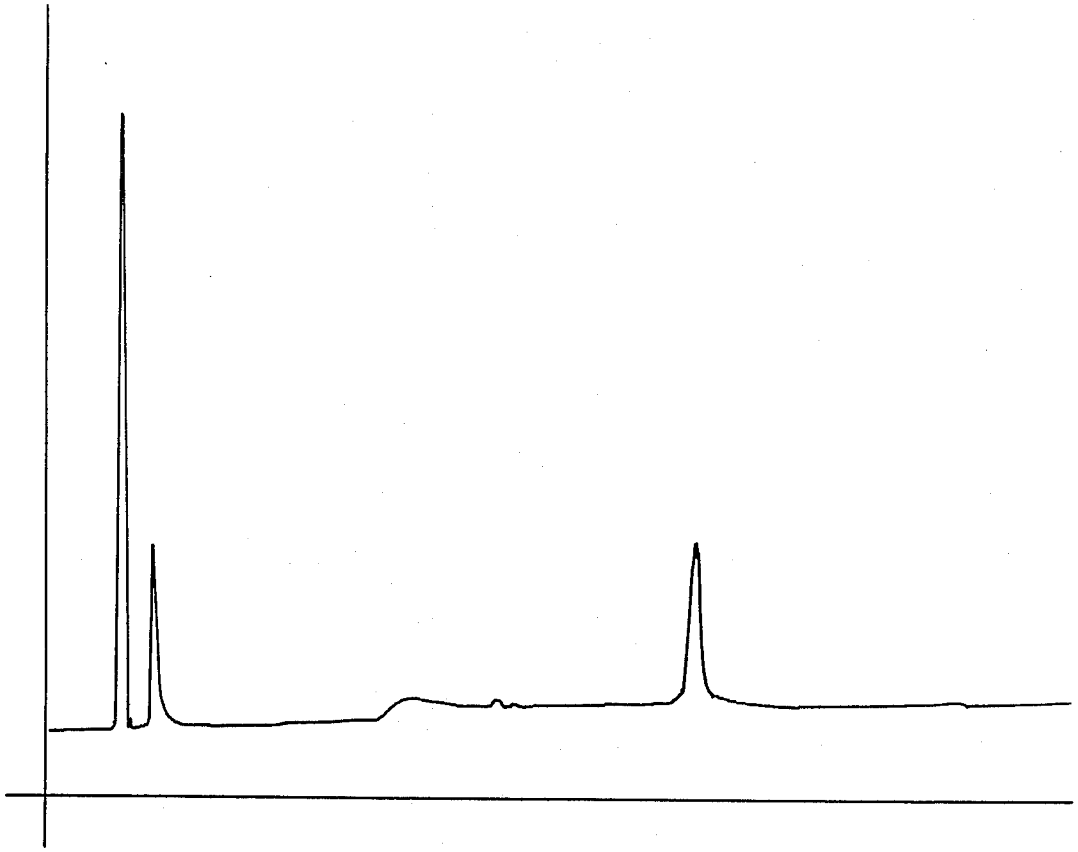

FIG. 13 is the GLC profile for the crude reaction product of Example V containing the compound having the structure:

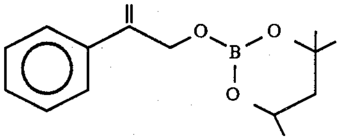

(Conditions: SE-30 column programmed at 100°-220° C. at 16° C. per minute).

Figure 14:
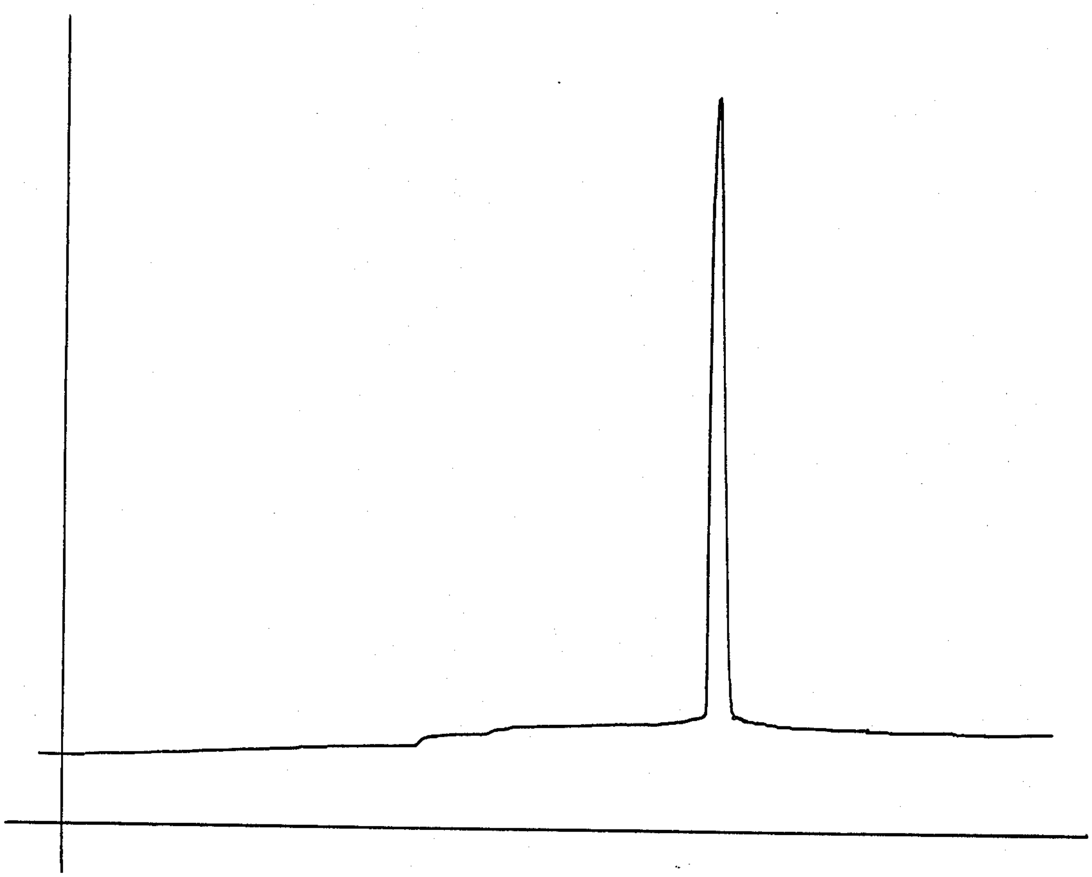

FIG. 14 is the GLC profile for bulked distillation fractions 4-8 of the distillation product of the reaction product of Example V containing the compound having the structure:

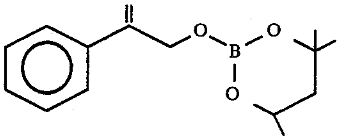

(Conditions: SE-30 column programmed at 100°-220° C. at 16° C. per minute).

Figure 15:
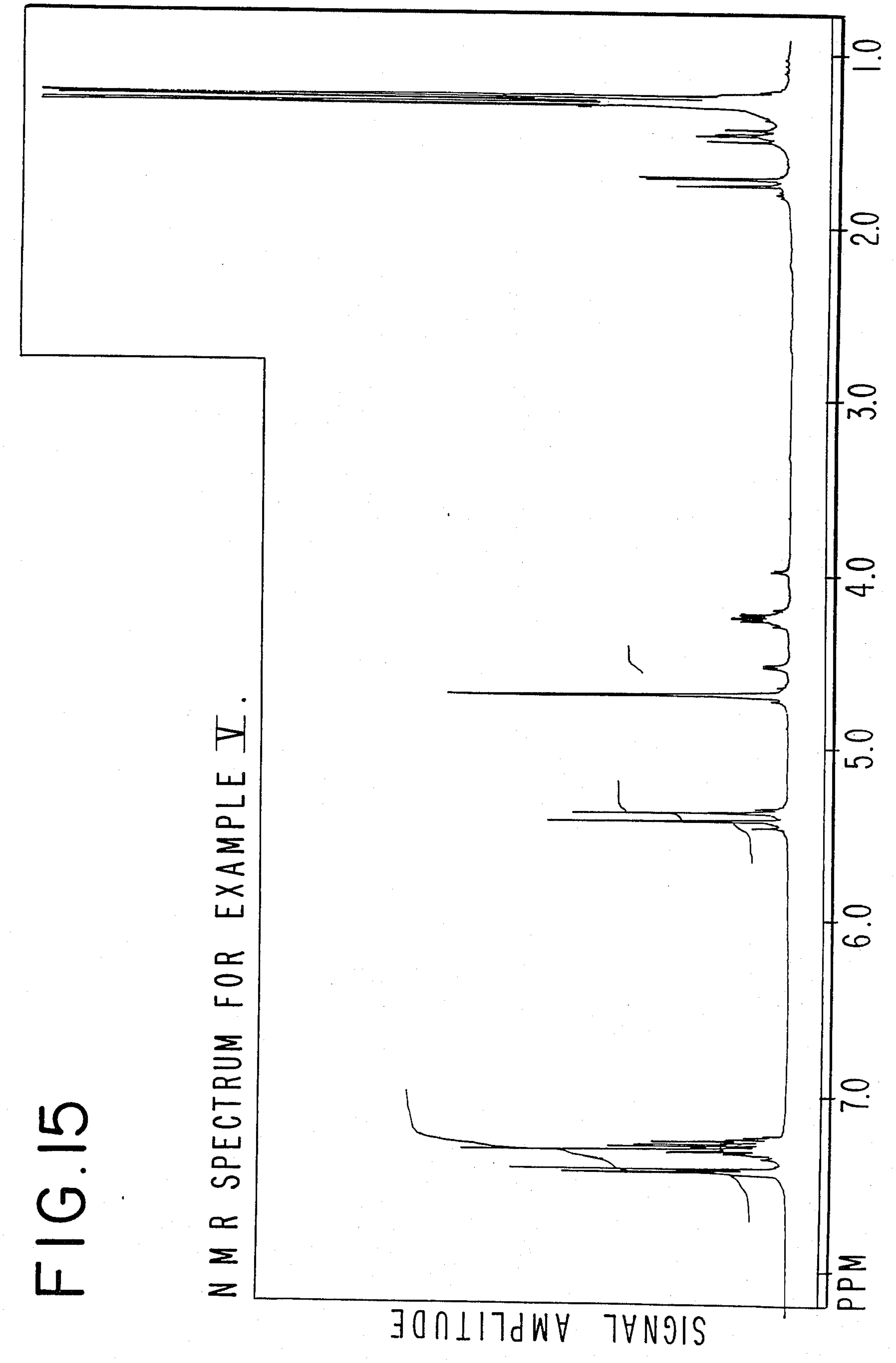

FIG. 15 is the NMR spectrum for the compound having the structure:

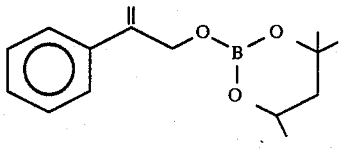

produced according to Example V.

Figure 16:
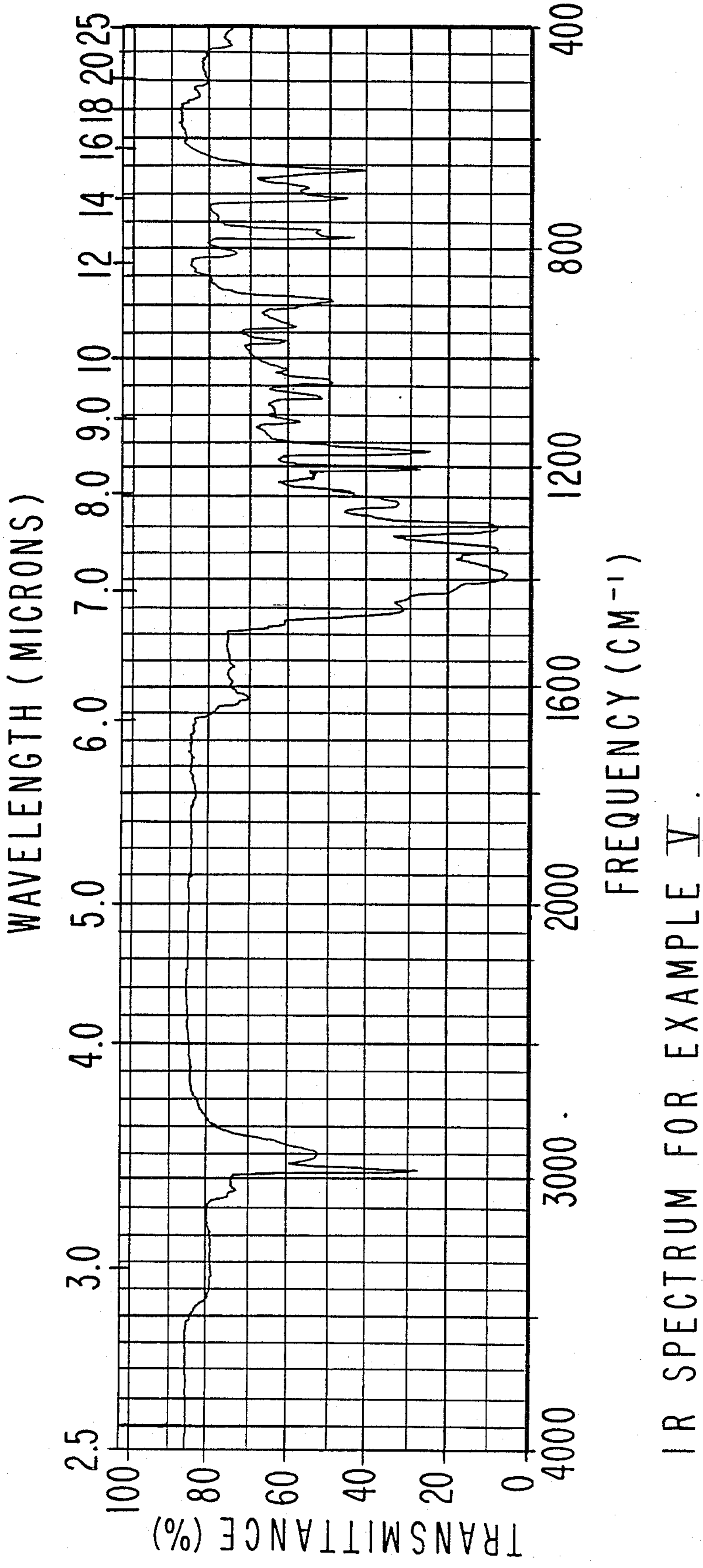

FIG. 16 is the infra-red spectrum for the compound having the structure:

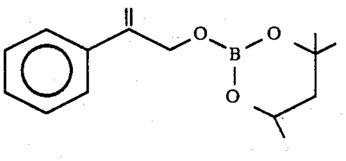

produced according to Example V.

Figure 17:
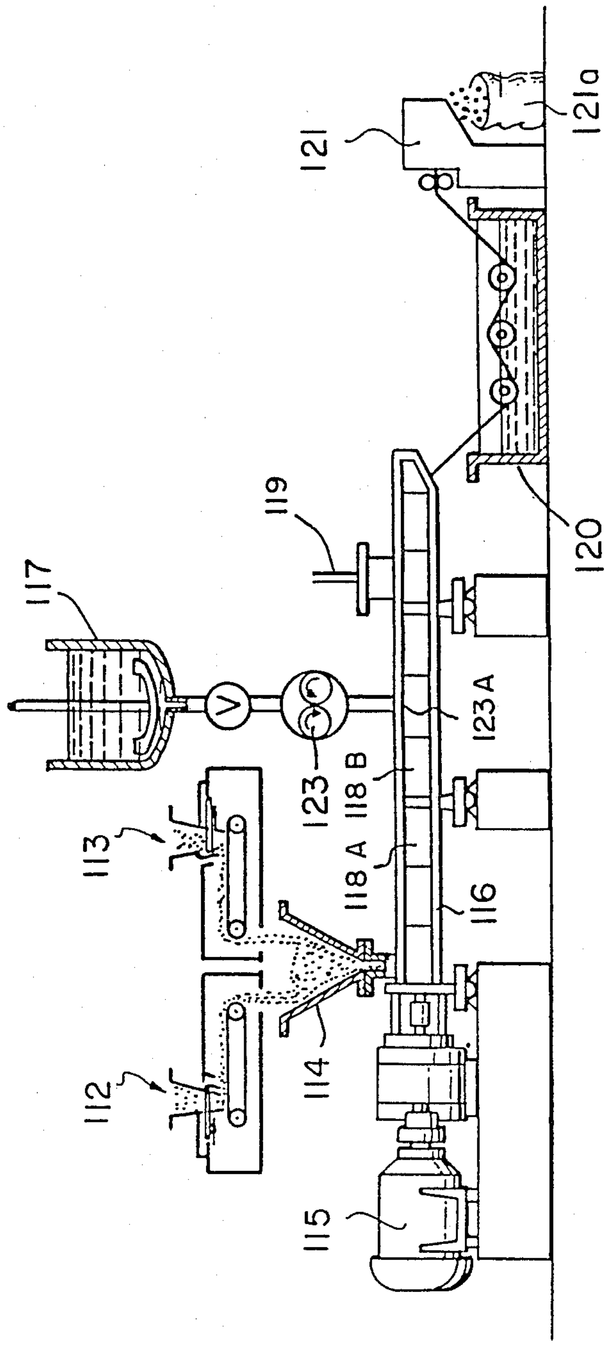

FIG. 17 is a cut-away side elevation schematic diagram of a screw extruder during the compounding of resin with one or more of the beta-alkylidene phenethyl alcohol esters and ethers of our invention while simultaneously adding foaming agent into a hollow portion of the barrel of the extruder and incorporates pelletizing apparatus used in pelletizing the extruded foam tow produced as a result of the extrusion operation.

DETAILED DESCRIPTION OF THE DRAWINGS

Figure 1:
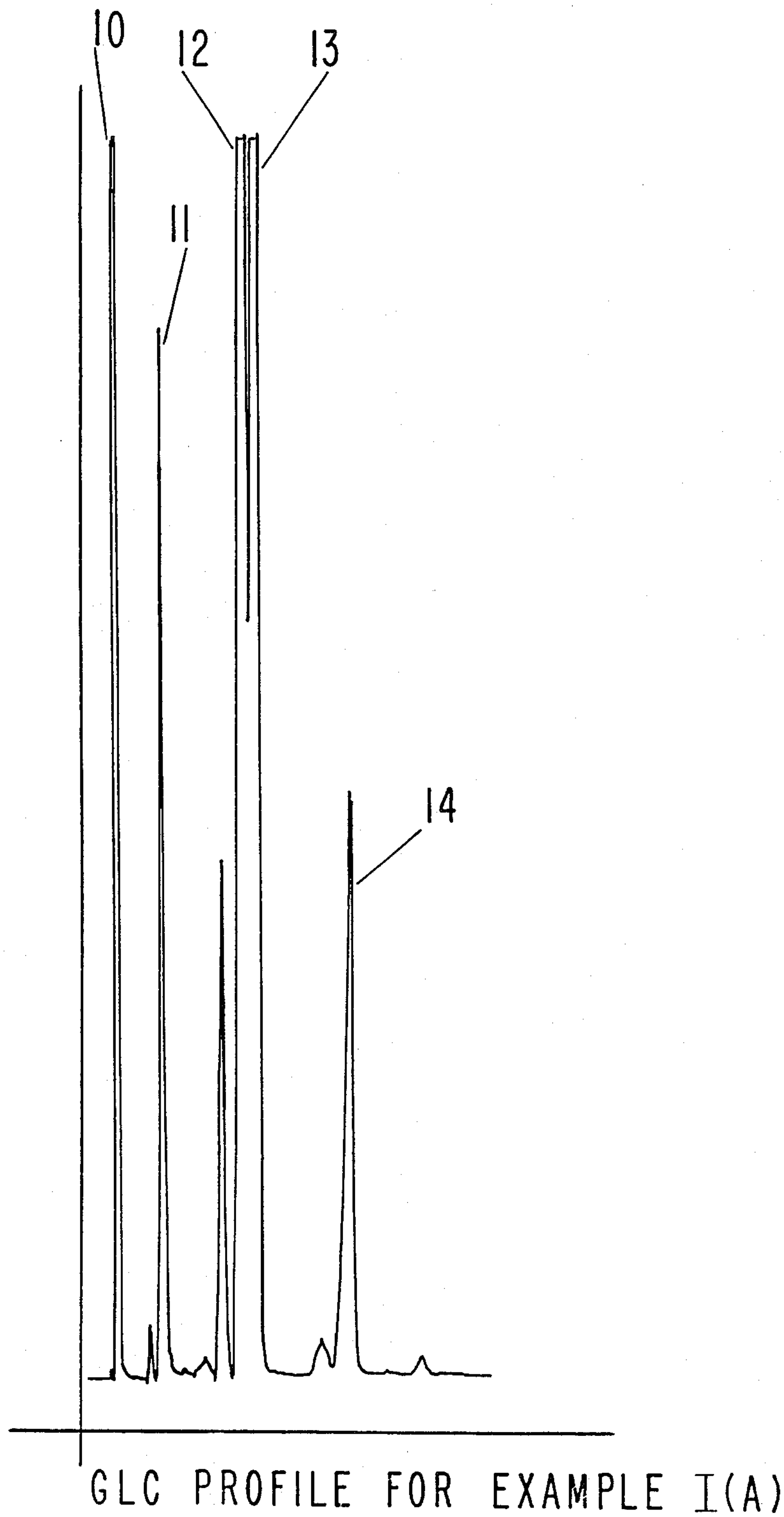
FIG. 1 is the GLC profile for the reaction product of Example I(A) containing the compounds having the structures.

FIG. 1 is the GLC profile for the reaction product of the first step of Example I(A) employing the reaction:

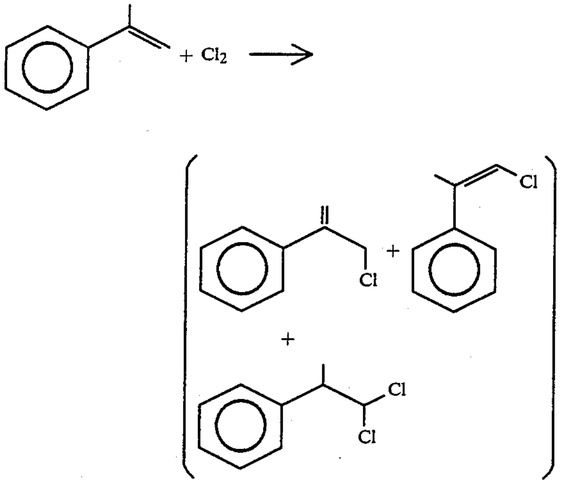

(Conditions: SE-30 column programmed at 180° C. isothermal). The peak indicated by reference numeral 10 is the peak for $CHCl_3$. The peak indicated by reference numeral 11 is the peak for the compounds having the structures:

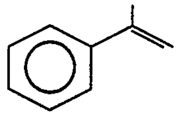
and
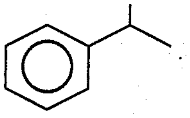
.

The peak indicated by reference numeral 12 is the peak for the compound having the structure:

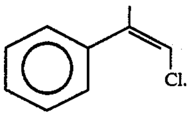

The peak indicated by reference numeral 13 is the peak for the compound having the structure:

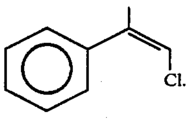

The peak indicated by reference numeral 14 is the peak for the compound having the structure:

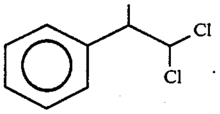

FIG. 3 is the GLC profile for the reaction product (second step) of Example I(A) resulting from the reaction:

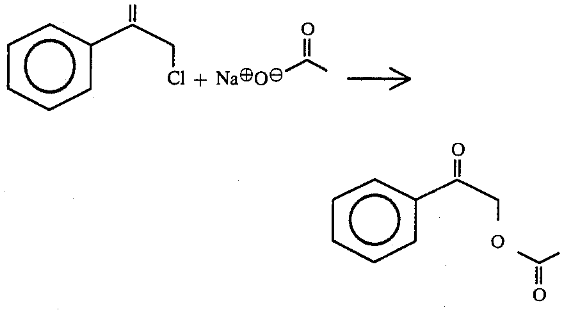

(Conditions: SE-30 column programmed at 180° C. isothermal).

The peak indicated by reference numeral 30 is the peak for $CHCl_3$. The peak indicated by reference numeral 31 is the peak for the compounds having the structures:

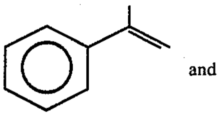
and
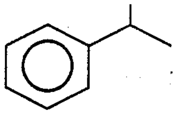
.

The peak indicated by reference numeral 32 is the peak for the compound having the structure:

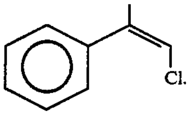

The peak indicated by reference numeral 33 is the peak for the compound having the structure:

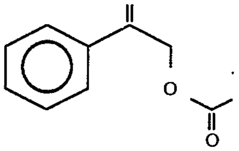

FIG. 5 is the GLC profile for the reaction product of Example I(B) the reaction being:

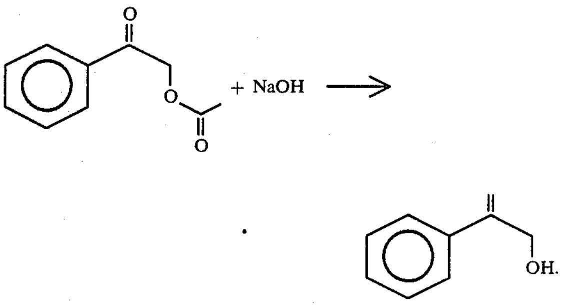

The peak indicated by reference numeral 50 is the peak for the compound having the structure:

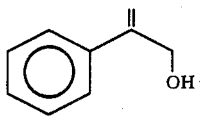

(Conditions: SE-30 column programmed at 180° C. isothermal).

FIG. 7 is the GLC profile for the reaction product (crude) of Example II, the reaction product resulting from the reaction:

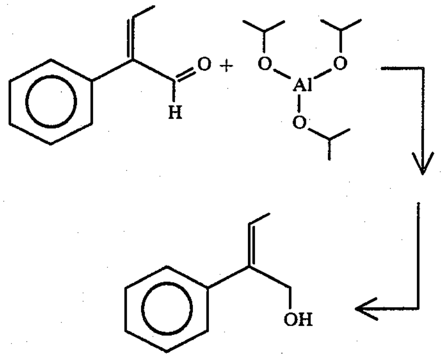

(Conditions: Carbowax column programmed at 180° C. isothermal). The peak indicated by reference numeral 70 is the peak for the compound having the structure:

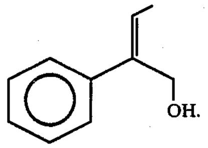

FIG. 9 is the GLC profile for the crude reaction product of Example III containing the compounds having the structures:

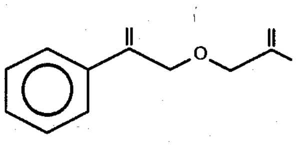
and
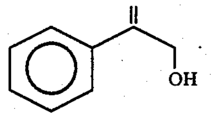

The peak indicated by reference numeral 91 is the peak for the compound having the structure:

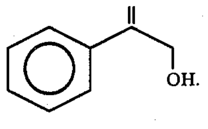

The peak indicated by reference numeral 92 is the peak for the compound having the structure:

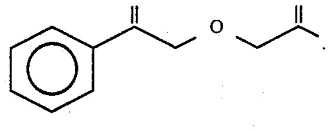

FIG. 11 is the GLC profile for the reaction product of Example IV. The peak indicated by reference numeral 1110 is the peak for the compound having the structure:

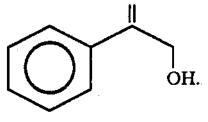

The peak indicated by reference numeral 1112 is the peak for the compound having the structure:

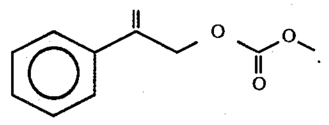

FIG. 17 is a schematic cut-away elevation diagram of extrusion and pelletizing apparatus useful in carrying out a process of our invention during the operation of said apparatus whereby perfuming material containing one of the beta-alkylidene phenethyl alcohol esters and ethers of our invention (and, optionally, at least one other perfumery ingredient) is incorporated into a resin such as polyethylene. Motor 115 drives the extruder screws located at 123A in barrel 116, the extruder being operated at temperatures in the range of from about 150° up to about 250° C. At the beginning of the barrel, resin at source 112 together with additives, e.g., opacifiers, processing aids, colors, pearlescent agents and densifiers at location 113 is added via additional funnel 114 into the extruder. Simultaneously (when the operation reaches "steady state"), a perfumant containing one of the beta-alkylidene phenethyl alcohol esters and ethers of our invention together with, optionally, at least one other perfumery ingredient, is added to the extruder at one, two or more of barrel segments 3–8 of the extruder (which may be a twin screw or single screw extruder) at locations 118*a,* 118*b,* 118*c* and 118*d* by means of gear pump 123 from source 117. From source 119 into barrel segments 5–10, gaseous or liquid blowing agents, e.g., nitrogen, carbon dioxide and the like are added simultaneously with the addition of the perfumant containing one or more of the beta-alkylidene phenethyl alcohol esters and ethers of our invention. The feed rate range of resin is about 80–300 pounds per hour. The feed rate range of the perfumant containing one or more of the beta-alkylidene phenethyl alcohol esters and ethers of our invention is between 1 and 35% of the feed rate range of the resin. The blowing agent rate range is such that the pressure of the gas or the pressure over the perfumant containing one or more of beta-alkylidene phenethyl alcohol esters and ethers of our invention being fed into the extruder is between about 50 and 200 psig. If desired, the extruded ribbon (122) or cylinder may be passed through a water bath 120 and pelletizer 121 into collection apparatus 121A.

THE INVENTION

It has now been determined that the beta-alkylidene phenethyl alcohol esters and ethers of our invention defined according to the structure:

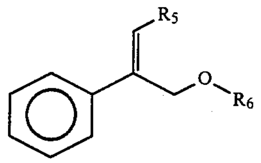

wherein $R_5$ represents hydrogen or methyl; wherein $R_6$ represents one of the moieties:

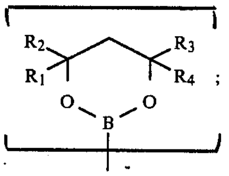

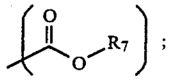

or

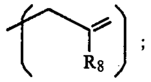

wherein $R_1$, $R_2$, $R_3$ and $R_4$ each represents the same or different hydrogen or methyl; wherein $R_7$ represents methyl or ethyl; and wherein $R_8$ represents hydrogen or methyl are capable of imparting or augmenting a variety of fragrances to various consumable materials including fragrance compositions, colognes, perfumed polymers and perfumed articles.

The beta-alkylidene phenethyl alcohol esters and ethers of our invention defined according to the generic structure:

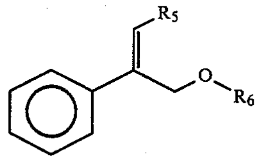

wherein $R_5$ represents hydrogen or methyl; wherein $R_6$ represents one of the moieties:

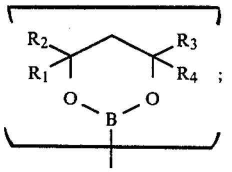

-continued

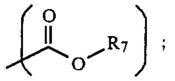

or

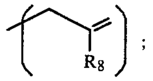

wherein $R_1$, $R_2$, $R_3$ and $R_4$ each represents the same or different hydrogen or methyl; wherein $R_7$ represents methyl or ethyl; and wherein $R_8$ represents hydrogen or methyl include the compounds having the structures:

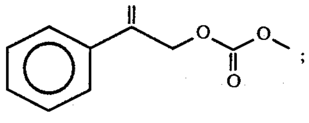

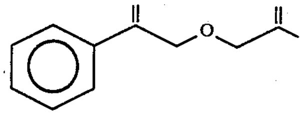

; and

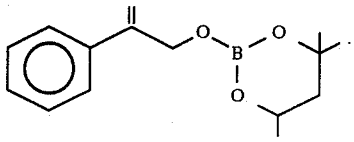

The compound having the structure:

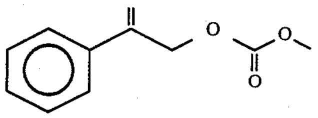

has a rose, lilac and spicy aroma with anisic topnotes. The compound having the structure:

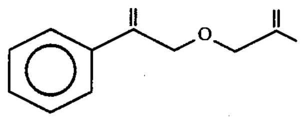

has a rose, ozoney and green aroma with a fruity topnote. The compound having the structure:

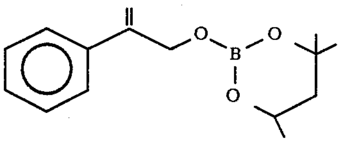

has a rose, cinnamon and carnation aroma with spicy, clove, lilac and piney topnotes.

Each of the compounds of our invention may be prepared by means of reaction of the compound having the structure:

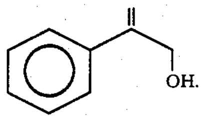

The compound having the structure:

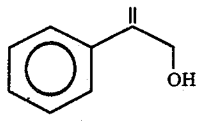

may be prepared by first reacting alpha-methyl styrene having the structure:

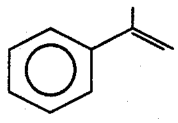

with a halogen such as chlorine according to the generic reaction:

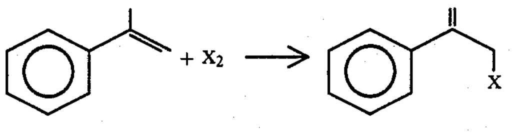

wherein X represents chloro or bromo (which includes the specific reaction and the preferred reaction:

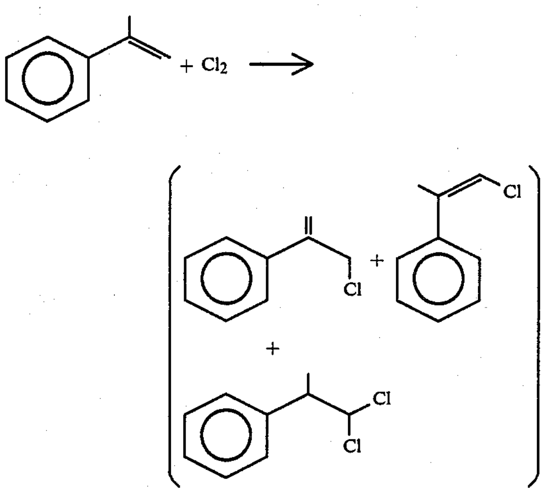

The resulting alpha-methylene phenethyl halide is then reacted with an alkali metal salt of an alkanoic acid according to the reaction:

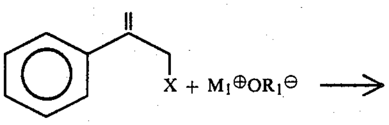

-continued

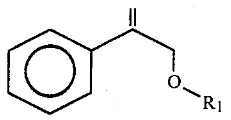

wherein X is chloro or bromo; $R_1$ represents $C_2$–$C_5$ acyl and $M_1$ represent alkali metal including sodium, potassium and lithium. The foregoing reaction includes the more specific reactions, to wit:

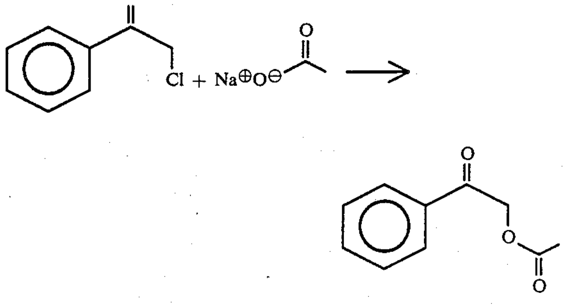

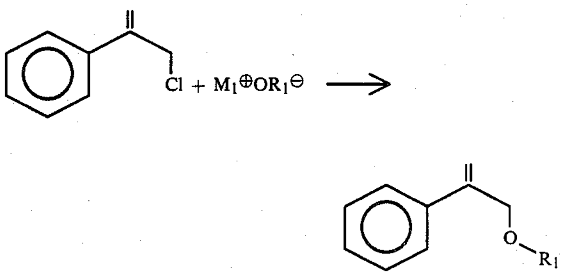

using the preferred chloro derivatives and using the preferred sodium acetate reactant.

The resulting ester having the structure:

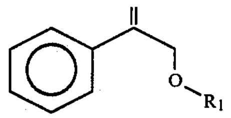

is then saponified with an alkali metal hydroxide according to the generic reaction:

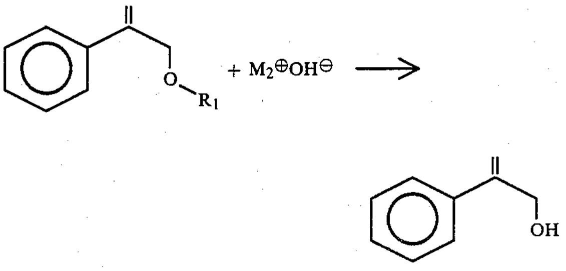

wherein $M_2$ is the same or different from $M_1$ and represents alkali metal including lithium, potassium or sodium. This generic reaction includes the specific reaction and the preferred reaction:

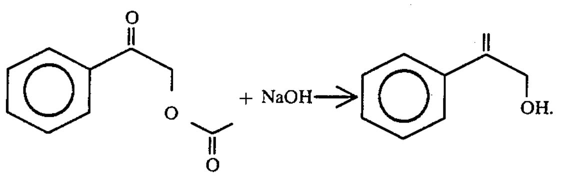

Another starting material is the compound having the structure:

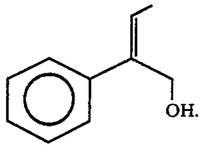

The compound having the structure:

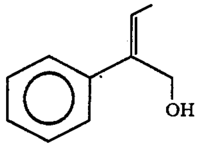

may be prepared by first reacting the aldehyde having the structure:

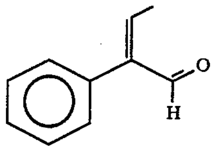

with an appropriate reducing agent, in this case aluminum triisopropylate according to the reaction:

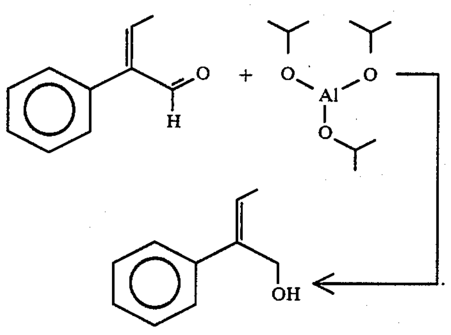

In carrying out the first part of the reaction leading towards the preparation of the compound having the structure:

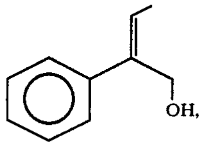

that is, the reaction, to wit:

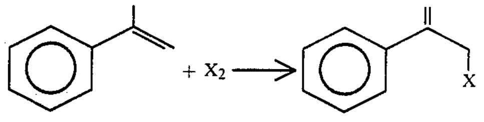

wherein X represents chloro or bromo, the reaction is carried out in the presence of an alkali metal carbonate such as and preferably sodium carbonate and in the presence of an inert solvent, preferably methylene dichloride. The reaction is carried out at a temperature in the range of from about 20° C. up to about 40° C. The halogen, e.g., the chlorine or the bromine is either fed (in the case of chlorine gas) or admixed (in the case of bromine liquid) into the mixture of the alkali metal carbonate, the alpha-methyl styrene and the methylene dichloride while maintaining the temperature in the range of 20°-40° C.

The second step of the reaction, to wit, the reaction:

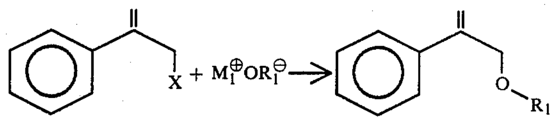

is carried out using an alkali metal acylate, preferably sodium acetate in the presence of a phase transfer agent such as an ALIQUAT ® phase transfer agent defined in U.S. Pat. No. 4,010,207 which ALIQUAT ® phase transfer agents are quaternary ammonium salts. This reaction takes place at a temperature in the range of from about 70° C. up to about 100° C.

The resulting ester product is defined according to the structure.

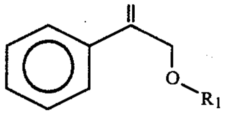

wherein $R_1$ represents $C_2$-$C_5$ acyl is then fractionally distilled and saponified using an alkali metal hydroxide such as sodium hydroxide preferably in the presence of a lower alkanol such as methyl alcohol. The reaction is carried out preferably at atmospheric pressure at reflux conditions, e.g., 90° C.-100° C. for a period of between about 2 and 6 hours. At the end of the reaction, the reaction product is washed with water and fractionally distilled yielding the product having the structure:

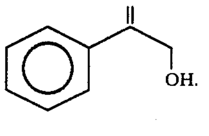

The compound having the structure:

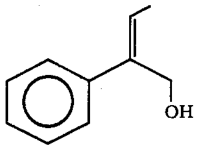

on the other hand is prepared according to the reaction:

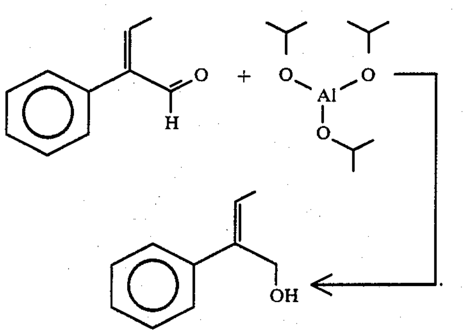

The aldehyde having the structure:

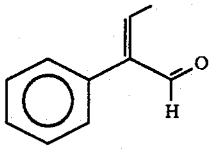

is reacted with aluminum triisopropylate at reflux conditions (e.g., about 110°-140° C.). Initially, the aluminum triisopropylate is admixed with isopropyl alcohol. The aldehyde having the structure:

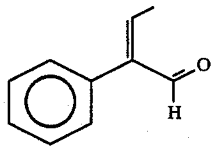

is then added to the aluminum triisopropylate mixture while the aluminum triisopropylate/isopropanol mixture is being refluxed. The reaction time varies from about 5 hours up to about 10 hours and the reaction temperature varies from about 110° C. up to about 140° C. At the end of the initial reaction, the reaction product is admixed with toluene and an aqueous alkali metal hydroxide such as 50% aqueous sodium hydroxide and the reaction mass is refluxed for a period of between about 0.5 hours up to about 2 hours. The reaction mass is then cooled to room temperature and washed with dilute base, e.g., 5% sodium hydroxide. The reaction mass is then distilled using a fractionation column at a vapor temperature in the range of 80°-90° C. and a pressure in the range of from about 2.1 up to about 2.5 mm/Hg.

With reference to the reaction, to wit:

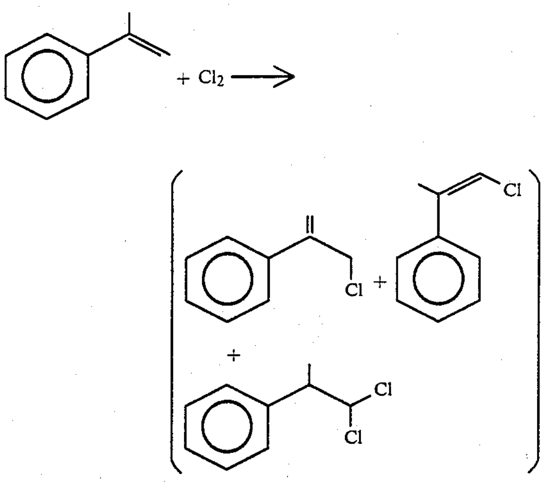

, the mole ratio of chlorine to alpha-methyl styrene may vary from about 1:1 down to about 0.5:1 and the temperature of this specific reaction may vary from about 0° C. up to about 50° C. The reaction may be carried out in a solvent or in the absence of a solvent. When a solvent is used a hydrocarbon or chlorocarbon solvent is useful. The reaction may be carried out in the presence of an alkali metal carbonate or bicarbonate, e.g., potassium carbonate, sodium carbonate, lithium carbonate, potassium bicarbonate, sodium bicarbonate or lithium bicarbonate.

With reference to the reaction, to wit:

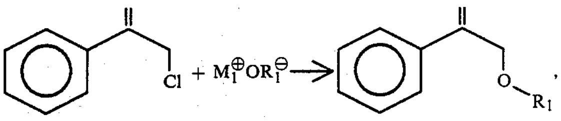

, $R_1$ may be acetyl, propenyl, butyryl or benzoyl. The phase transfer agent is a quaternary ammonium salt such as ALIQUAT ® 336 marketed by the Henkel Corporation of Minneapolis, Minn. and more fully described in U.S. Pat. No. 4,010,207. This reaction is preferably carried out at reflux conditions in a solvent or in the absence of a solvent.

With respect to the reaction:

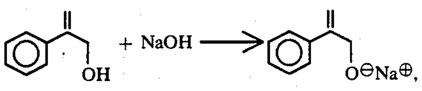

, this reaction is carried out using 1.2 up to 2 equivalents of an alkali metal hydroxide such as sodium hydroxide or potassium hydroxide (10-30% in water) and may be carried out in the presence of a solvent or in the absence of a solvent, said solvent being, for example, a lower alkanol such as methyl alcohol or ethyl alcohol as stated, supra.

The compounds having the structure:

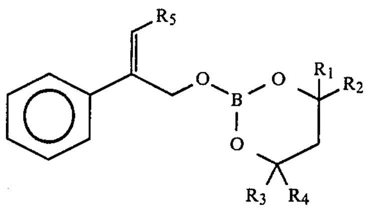

may be prepared by reacting the compound having the structure:

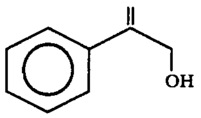

or the compound having the structure:

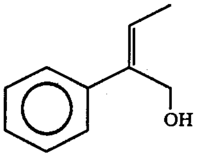

with one or more compounds having the genus:

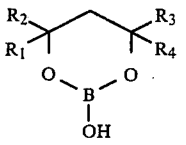

according to the reaction:

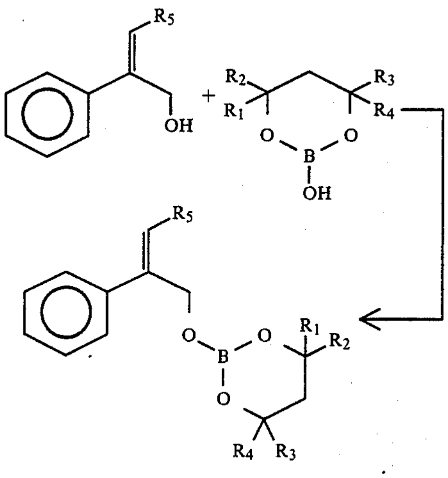

which includes the reaction:

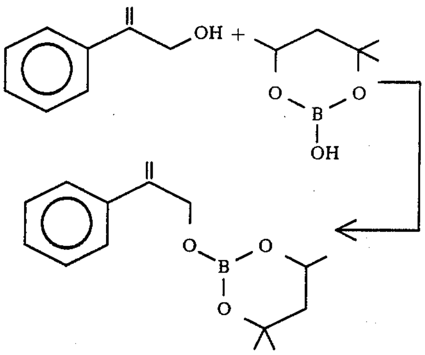

The compound having the structure:

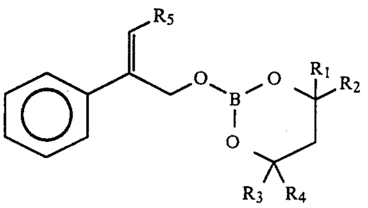

thus produced can also be used to augment or enhance or impart aroma to or in perfume compositions, colognes, perfumed polymers and perfurmed articles including solid or liquid anionic, cationic, nonionic or zwitterionic detergents and fabric softener composition and fabric softener articles, including drier-added fabric softener articles as a result of hydrolysis of compounds having the generic structure:

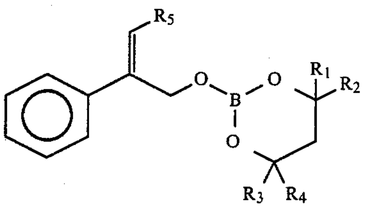

whereby substantially pure versions of compounds having the structures:

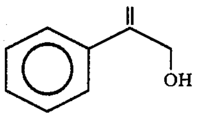

and

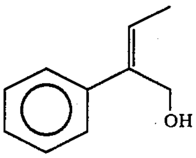

are created subsequent to such hydrolysis according to the hydrolysis reaction:

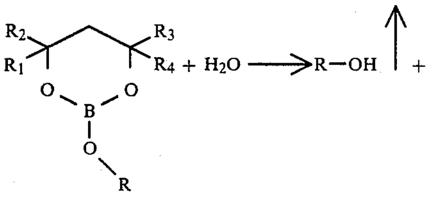

-continued

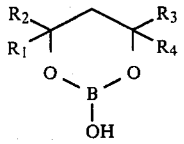

wherein R is the residue of one of the compounds:

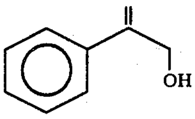

and

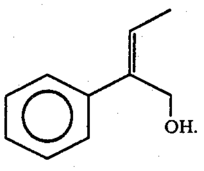

The hydrolysis of members of the genus defined according to the structure:

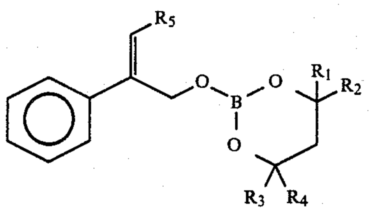

takes place as a result of the utilization of the perfume composition, cologne, perfumed article or perfumed polymer e.g., when another article with which the perfume composition, perfumed article, cologne or perfumed polymer is contacted with water or water vapor.

As a result of the hydrolysis of one or more compounds which is a member of the genus of compounds having the structure:

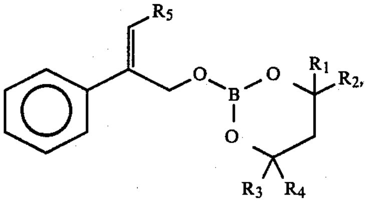

one or more of the compounds having the structure:

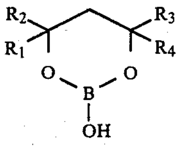

are formed and do not hydrolyze any further but are either washed away or volatilized without causing any adverse reaction:

(i) with the article or composition or polymer to which the aroma is intended to be imparted; or (ii) to the user of the perfume composition or cologne.

By the same token the other hydrolysis products, namely the alcohols, to wit:

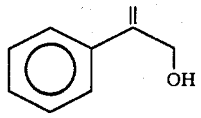

and

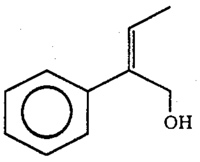

are also volatilized on use thereof without any adverse reaction to the article or polymer on which it (they) is (are) used or to the user of the perfume composition or cologne.

The compounds defined according to the generic structure:

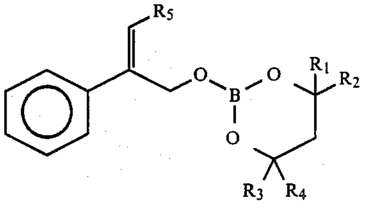

are prepared by first reacting boric acid with a 1,3-glycol having the generic structure:

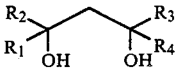

(wherein $R_1$, $R_2$, $R_3$ and $R_4$ are defined, supra (for example, the glycol having the structure:

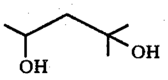

according to the reaction:

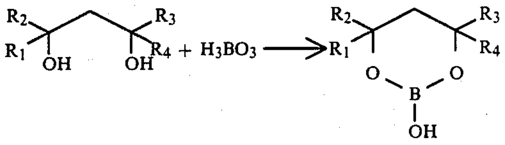

(wherein $R_1$, $R_2$, $R_3$ and $R_4$ are defined, supra) whereby the compound of the genus having the structure:

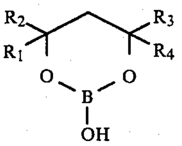

is formed.

The genus of compounds having the structure:

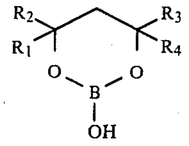

is then reacted with one of the alcohols having one of the structures:

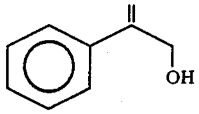
or
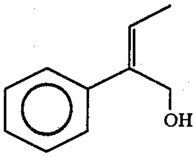

according to the reaction:

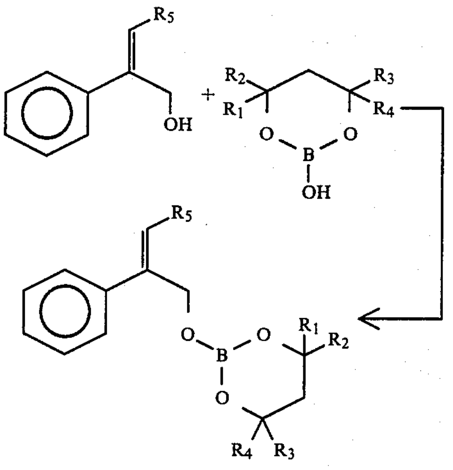

in order to form the genus of compounds defined according to the structure:

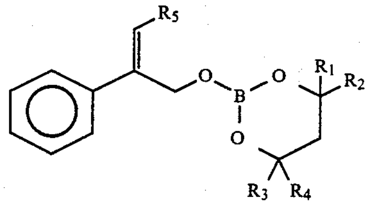

The mole ratio of boric acid:glycol having the structure:

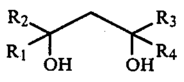

is approximately 1:1. The mole ratio of compound having the structure:

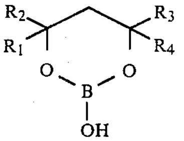

to alcohol having one of the structures:

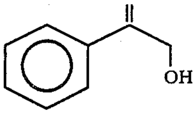
or
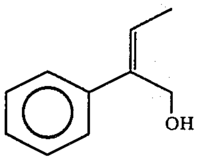

is also approximately 1:1.

The first reaction, to wit:

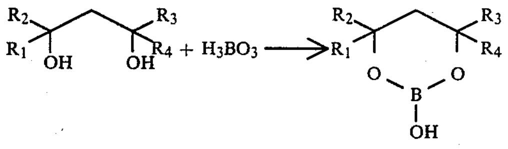

takes place in the presence of an inert solvent such as toluene. The concentration of glycol having the structure:

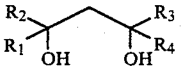

in the toluene is between 6 and 10 moles per liter of reaction mass.

The reaction takes place at approximately 110°-120° C. and water of reaction is constantly removed using, for example, a Dean Stark trap.

At the end of the reaction, the reaction mass is cooled and admixed with alcohol defined according to one of the structures:

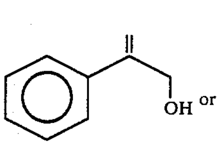
or
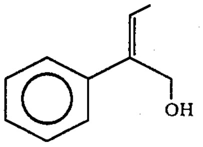

so that the reaction:

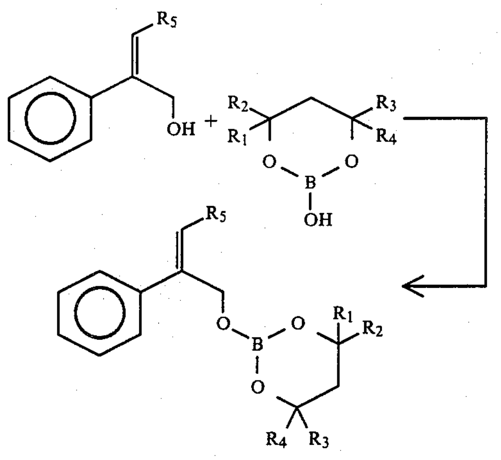

may proceed. The second reaction is carried out at reflux conditions at a temperature in the range of from about 70°-100° C. for a period of time of between 1 and about 5 hours until anaylsis indicates completion of the reaction (when all of the water of reaction is evolved).

The second reaction may be carried out in the absence of solvent or in the presence of an inert solvent such as cyclohexane or any other inert solvent having a boiling point which will enable the reaction to proceed in a reasonable period of time and yielding a reasonable yield of reaction product.

At the end of the reaction, the reaction mass is fractionally distilled. Indeed, an advantage of our invention is the fact that a member of the genus of compounds having the structure:

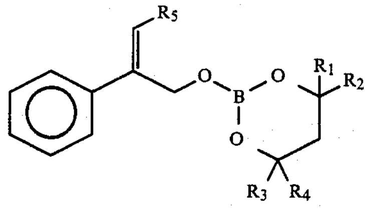

is stable under all reaction conditions and is only decomposible in water; and then only decomposible into one of the alcohols having the structures:

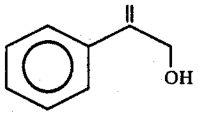
and
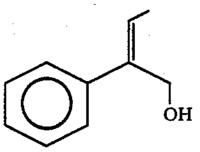

and the compound having the structure:

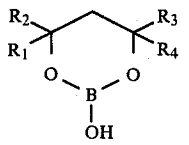

according to the reaction:

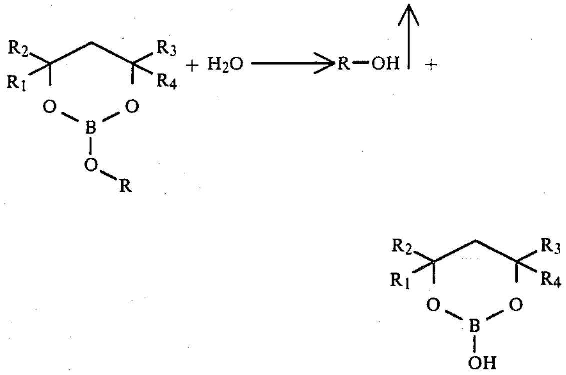

wherein R is a residue of one of the alcohols:

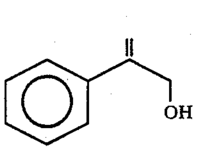
or
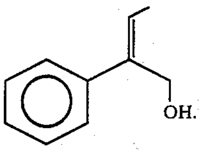

The compounds defined according to the structure:

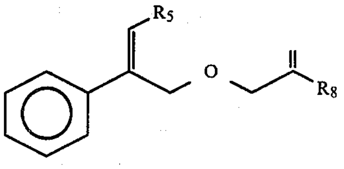

including the compound having the structure:

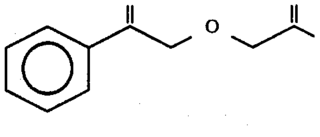

may be prepared by reacting one of the alcohols having the structures:

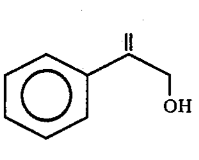
or
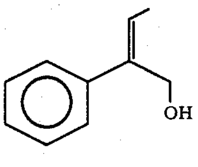

within an alkali metal hydroxide or an alkaline earth metal hydroxide according to the generic reaction:

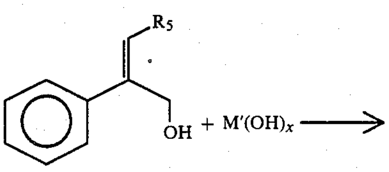

-continued

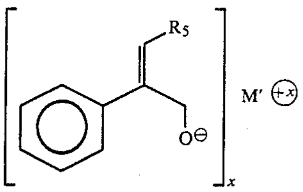

wherein x is 1 or 2 and wherein M represents alkali metal or alkaline earth metal which includes the reaction:

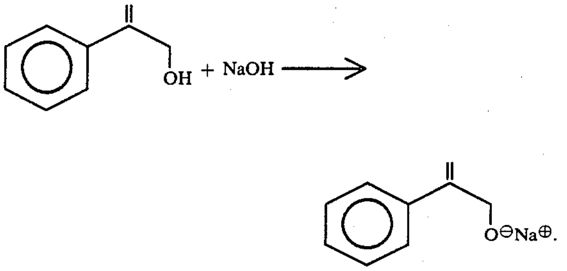

The resulting salt is then reacted with an allyl halide according to the reaction:

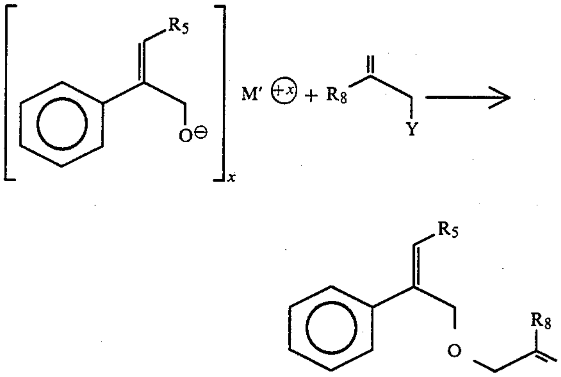

wherein $R_8$ is hydrogen or methyl and wherein Y is chloro or bromo including the reaction:

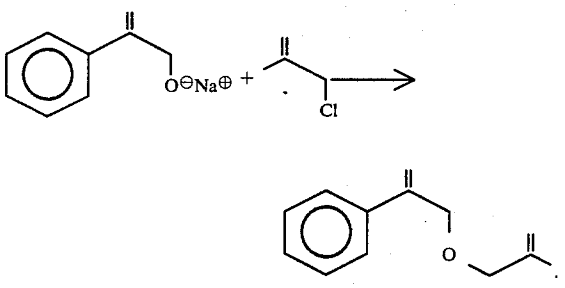

The conditions for such ether formation are well known to one having ordinary skill in the art.

The carbonates defined according to the generic structure:

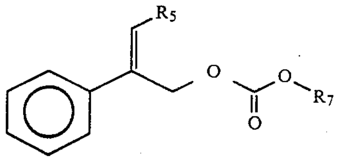

may be prepared by reacting one of the alcohols defined according to one of the structures:

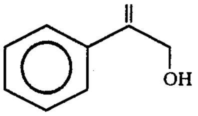
or
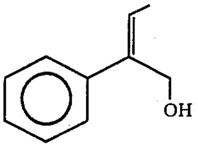

with a dialkyl carbonate according to the reaction:

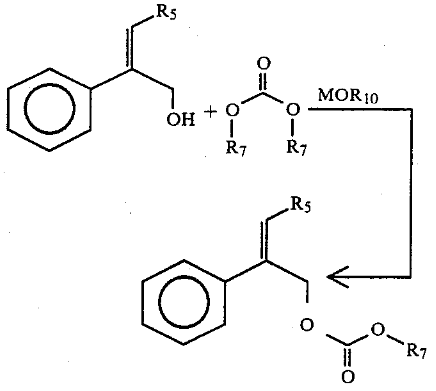

wherein M represents alkali metal such as sodium or potassium; wherein $R_{10}$ represents lower alkyl, e.g., methyl or ethyl; and wherein $R_7$ represents methyl or ethyl, including the reaction:

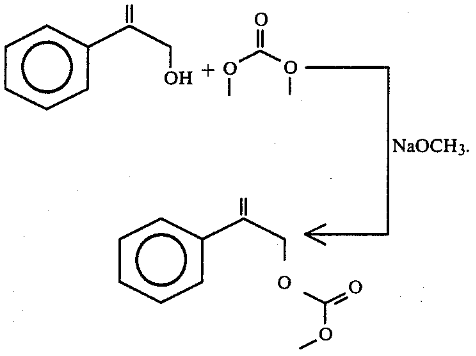

The conditions for forming such a carbonate are well known to one having ordinary skill in the art; and are exemplified, infra.

It will be appreciated from the present disclosure that the beta-alkylidene phenethyl alcohol esters and ethers of our invention can be used t alter, vary, fortify, modify, enhance or otherwise improve the aroma of a wide variety of materials particularly including perfume compositions, perfumed articles and perfumed polymers.

Thus, the beta-alkylidene phenethyl alcohol esters and ethers of our invention can be used to contribute materials which can provide rose, cinnamon, carnation, lilac, spicy, ozoney and green aromas with spicy, clove, lilac, piney, anisic and fruity topnotes to perfume compositions, perfumed articles and perfumed polymers.

As olfactory agents the beta-alkylidene phenethyl alcohol esters and ethers of our invention can be formulated into or used as components of a "perfume composition".

The "perfume composition" is used herein to mean a mixture of organic compounds, including, for example, alcohols other than the alcohols of this invention, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristic but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of beta-alkylidene phenethyl alcohol esters and ethers of our invention which will be effective in perfume compositions depends on many factors, including the other ingredients, their amounts and the effects which are desired. It has been found that perfume compositions containing as little as 0.05% and as much as 50% of the beta-alkylidene phenethyl alcohol esters and ethers of our invention can be used to impart, augment or enhance materials which can provide rose, cinnamon, carnation, lilac, spicy, ozoney and green aromas with spicy, clove, lilac, piney, anisic and fruity topnotes in soaps, cosmetics, solid or liquid anionic, cationic, nonionic or zwitterionic detergents and other products. The amount employed can range up to 70% of the fragrance and can be as low as 1% of the original fragrance and will depend on considerations of cost, nature of the end product, the effect desired in the finished product and the particular fragrance sought.

The beta-alkylidene phenethyl alcohol esters and ethers of our invention can be used alone or in a perfume composition as an olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powders, and the like.

When used as an olfactory component of a perfumed article, as little as 0.05% of one or more of the beta-alkylidene phenethyl alcohols of our invention will suffice to impart materials which can provide rose, cinnamon, carnation, lilac, spicy, ozoney and green aromas with spicy, clove, lilac, piney, anisic and fruity topnotes. Generally no more than 5.0% is required based on the perfumed article. Accordingly, the range in the perfumed article may vary from about 0.05% up to about 5.0% of the beta-alkylidene phenethyl alcohols of our invention.

In addition, the perfume composition can contain a vehicle or carrier for the beta-alkylidene phenethyl alcohols taken alone or together with other ingredients. The vehicle can be a liquid such as an alcohol such as ethanol, a glycol such as propylene glycol, or the like. The carrier can be an absorbent solid such as gum or a microporous polymer or components for encapsulating the composition such as by means of coacervation.

The following Examples I(A), I(B) and II are given to illustrate techniques for producing the beta-alkylidene phenethyl alcohol esters and ethers of our invention. The examples following Example II, that is, Examples III and onward are given to illustrate embodiments of our invention as it is presently preferred to practice it insofar as utilizing the beta-alkylidene phenethyl alcohol esters and ethers of our invention for their organoleptic properties. It will be understood that these examples are illustrative and the invention is not to be considered restricted thereto except as indicated in the appended claims.

EXAMPLE I

Preparation of Beta-Methylene Phenethyl Alcohol

EXAMPLE I(A), STEP 1

Reaction:

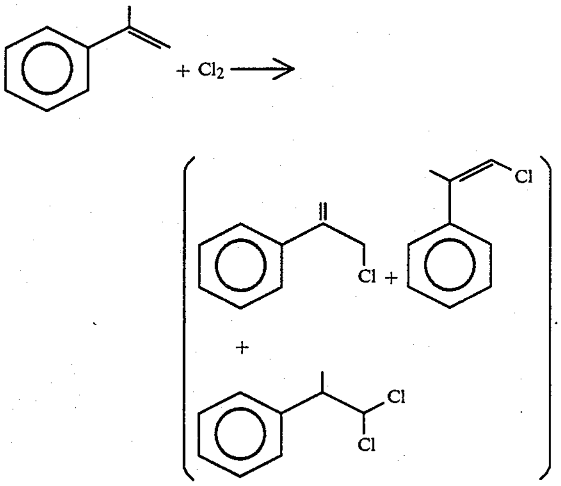

Into a 2 liter reaction vessel equipped with stirrer, thermometer, reflux condenser and chlorine feed line are placed 190 grams of sodium carbonate, 420 grams of alpha-methyl styrene and 400 ml of methylene dichloride. While maintaining the reaction mass at 25° C., chlorine gas is fed into the reaction mass over a period of one hour (with carbon dioxide evolution). At the end of the one hour chlorine feed time, the reaction mass is washed with water for use in Step 2.

FIG. 1 is the GLC profile for the reaction product of Step 1. The peak indicated by reference numeral 10 is the peak for $CHCl_3$. The peak indicated by reference numeral 11 is the peak for the compounds having the structures:

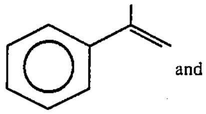 and 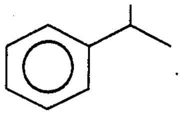.

The peak indicated by reference numeral 12 is the peak for the compound having the structure:

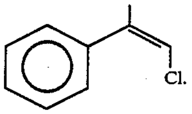

The peak indicated by reference numeral 13 is the peak for the compound having the structure:

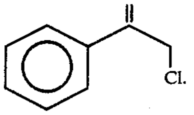

The peak indicated by reference numeral 14 is the peak for the compound having the structure:

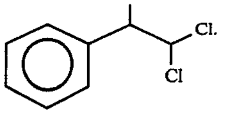

FIG. 2 is the NMR spectrum for the reaction product of Example I(A), a trap of peaks 12 and 13 of FIG. 1. The NMR spectrum is thus for the compounds having the structures:

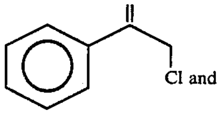 and 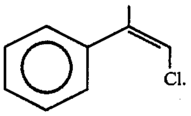

The weight ratio of compound having the structure:

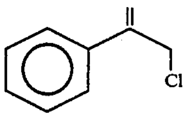

to the compound having the structure:

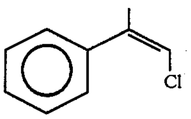

is approximately 3:2.

EXAMPLE I(A), STEP 2

Reaction:

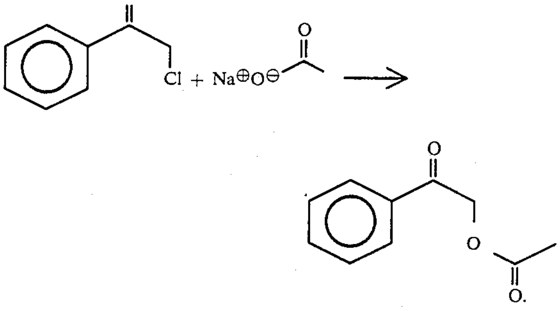

Into a 1 liter reaction vessel equipped with reflux condenser, thermometer and heating mantle is placed the organic phase of Step 1, supra containing the compounds having the structures:

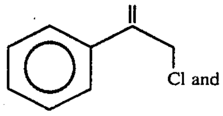 and 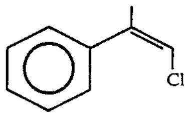

and in addition 291 grams of sodium acetate and 15 grams of ALIQUAT 336®. The reaction mass is heated to 80° C. and maintained at 80° C. for a period of one hour. At the end of the one hour period, the reaction mass is distilled on an 18" Goodloe column yielding the following fractions:

| Fraction No. | Vapor Temp. (°C.) | Liquid Temp. (°C.) | Vacuum mm/Hg. Pressure | % Acetate |
|---|---|---|---|---|
| 1 | 23/65 | 23/88 | 120/10 | — |
| 2 | 70 | 92 | 12.0 | — |
| 3 | 70 | 94 | 12.0 | — |
| 4 | 73 | 96 | 12.0 | — |
| 5 | 74 | 100 | 12.0 | 1 |
| 6 | 85 | 101 | 10.0 | 16 |
| 7 | 75 | 108 | 10.0 | — |
| 8 | 75 | 100 | 10.0 | 47 |
| 9 | 75 | 108 | 10.0 | 75 |
| 10 | 99 | 113 | 10.0 | 73 |
| 11 | 100 | 113 | 10.0 | 69 |
| 12 | 100 | 113 | 10.0 | 73 |
| 13 | 100 | 113 | 10.0 | 76 |
| 14 | 102 | 113 | 11.0 | — |
| 15 | 102 | 113 | 12.0 | — |
| 16 | 102 | 113 | 12.0 | — |
| 17 | 102 | 113 | 16.0 | — |
| 18 | 102 | 113 | 10.0 | — |
| 19 | 102 | 113 | 10.0 | 97 |
| 20 | 100 | 110 | 8.0 | — |
| 21 | 100 | 108 | 8.0 | — |
| 22 | 90 | 108 | 4.5 | 99 |
| 23 | 90 | 108 | 4.5 | 100 |
| 24 | 88 | 107 | 4.2 | 100 |
| 25 | 88 | 107 | 4.1 | 100 |
| 26 | 88 | 107 | 4.0 | 100 |
| 27 | 88 | 108 | 4.0 | 100 |
| 28 | 88 | 109 | 3.9 | 100 |
| 29 | 88 | 112 | 3.9 | 100 |
| 30 | 88 | 118 | 3.9 | 100 |
| 31 | 90 | 139 | 4.2 | 100 |
| 32 | 90 | 165 | 6.0 | — |
| 33 | 88 | 180 | 4.0 | —. |

Fractions 22–31 are bulked for use in Example I(B).

FIG. 3 is the GLC profile for the reaction product of Step 2 of this Example I(A). The peak indicated by reference numeral 30 is the peak for $CHCl_3$. The peak indicated by reference 31 is the peak for the compounds having the structures:

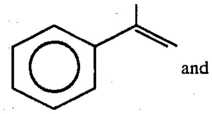
and
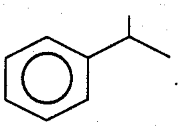

The peak indicated by reference numeral 32 is the peak for the compound having the structure:

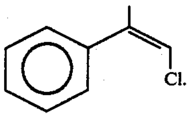

The peak indicated by reference numeral 33 is the peak for the compound having the structure:

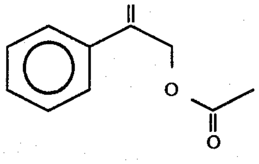

(Conditions: SE-30 column programmed at 180° C. isothermal).

The peak indicated by reference numeral 33 on FIG. 3 is trapped. FIG. 4 is the NMR spectrum for the peak indicated by reference numeral 33 on FIG. 3 and is for the compound having the structure:

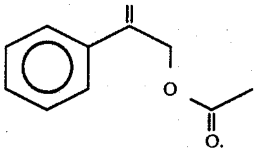

EXAMPLE I(B)

Reaction:

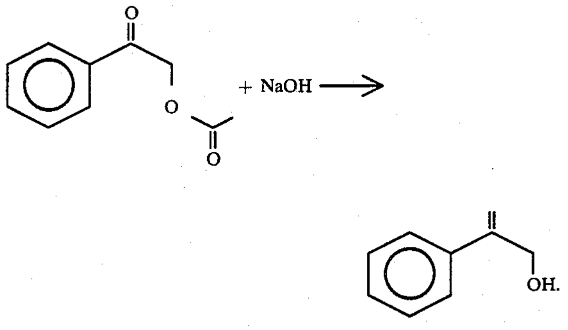

Into a 2 liter reaction vessel equipped with stirrer, thermometer, reflux condenser and heating mantle are placed 500 grams of the reaction product of Example I(A) containing the compound having the structure:

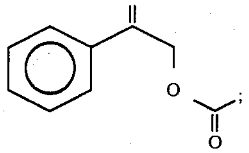

320 grams of an aqueous solution of 50% sodium hydroxide; 80 grams of water and 150 grams of methyl alcohol. The reaction mass is heated to reflux (temperature=92° C.) and maintained at reflux for a period of four hours. At the end of the four hour period, the reaction mass is cooled to room temperature and washed with water. The organic phase is then distilled on a Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 27/25 | 23/110 | 150/4 | 100% |
| 2 | 80 | 100 | 4.1 | 9:1 |
| 3 | 88 | 100 | 3.5 | 9:1 |
| 4 | 88 | 100 | 3.5 | 9:1 |
| 5 | 88 | 100 | 3.5 | 4:1 |
| 6 | 88 | 100 | 3.5 | 4:1 |
| 7 | 88 | 100 | 3.5 | 4:1 |
| 8 | 88 | 100 | 3.5 | 4:1 |
| 9 | 78 | 100 | 3.5 | 3:1 |
| 10 | 78 | 100 | 3.5 | 3:1 |
| 11 | 88 | 100 | 3.5 | 3:1 |
| 12 | 80 | 118 | 3.5 | 3:1 |
| 13 | 80 | 168 | 3.5 | — |

The resulting product has a lilac, rose, hyacinth, peony, green, cinnamon and honey aroma with intense green, lilac, rose and hyacinth undertones. Of particular interest is the "natural" floral nuance of this material.

FIG. 5 is the GLC profile of the crude reaction mixture. The peak indicated by reference numeral 50 is the peak for the compound having the structure:

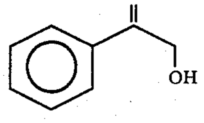

(Conditions: SE-30 column programmed at 180° C. isothermal).

FIG. 6 is the NMR spectrum for the compound having the structure:

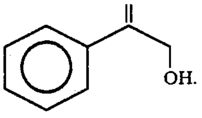

EXAMPLE II

Preparation of Beta-Ethylidene Phenethyl Alcohol

Reaction:

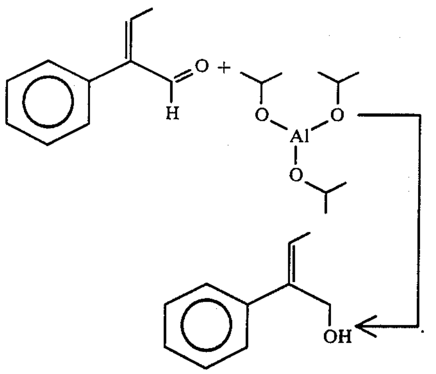

Into a 3 liter reaction vessel equipped with stirrer, reflux condenser, thermometer and heating mantle are placed 2000 grams of isopropyl alcohol and 75 grams of aluminum triisopropylate. The resulting mixture is heated to reflux and while refluxing, over a period of 1.5 hours, 500 grams of the aldehyde having the structure:

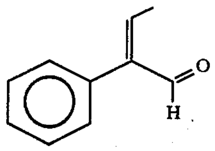

is added slowly to the reaction mass. At the end of the feed period of the aldehyde, solvent is commenced to be stripped at the ratio of 3:1 to a pot temperature of 130° C. The stripping takes place over a period of 5.5 hours. At the end of the 5.5 hour period, the reaction mass is cooled to 80° C. and 500 ml toluene and 150 grams of 50% aqueous sodium hydroxide and 150 grams of water is added to the reaction mass. The reaction mass is refluxed for a period of one hour and then cooled to room temperature.

The reaction mass is washed with 5% aqueous sodium hydroxide and the organic phase is distilled yielding the following fractions (on a Goodloe column):

| Fraction No. | Vapor Temp. (C.) | Liquid Temp. (C.) | Vacuum mm/Hg. Pressure | Reflux Ratio |
|---|---|---|---|---|
| 1 | 23/25 | 23/115 | 200/4 | 100% |
| 2 | 85 | 103 | 2.4 | 9:1 |
| 3 | 85 | 103 | 2.4 | 9:1 |
| 4 | 87 | 103 | 2.4 | 9:1 |
| 5 | 87 | 103 | 2.4 | 9:1 |
| 6 | 87 | 103 | 2.4 | 9:1 |
| 7 | 87 | 103 | 2.4 | 9:1 |
| 8 | 87 | 103 | 2.4 | 9:1 |
| 9 | 87 | 105 | 2.4 | 9:1 |
| 10 | 83 | 106 | 2.2 | 9:1 |
| 11 | 84 | 106 | 2.2 | 9:1 |
| 12 | 82 | 108 | 2.2 | 4:1 |
| 13 | 82 | 108 | 2.2 | 4:1 |
| 14 | 82 | 110 | 2.2 | 4:1 |
| 15 | 81 | 115 | 2.2 | 4:1 |
| 16 | 81 | 132 | 2.2 | 4:1 |
| 17 | 80 . | 180 | 2.2 | 4:1. |

FIG. 7 is the GLC profile for the reaction product of this example containing the compound having the structure:

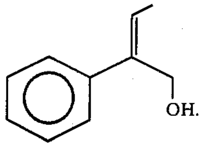

The peak indicated by reference numeral 70 is the peak for the compound having the structure:

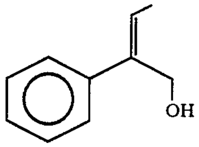

(Conditions: Carbowax column programmed at 180° C. isothermal).

FIG. 8 is the NMR spectrum for the compound having the structure:

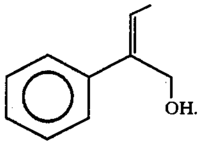

The compound having the structure:

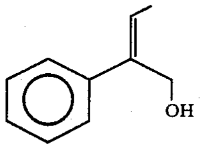

has an excellent aesthetically pleasing green, floral aroma with green and rose undertones.

EXAMPLE III

Preparation of the Alpha-Methylene Phenylethyl Alcohol Methallyl Ether

Reactions

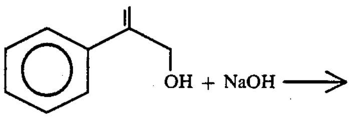

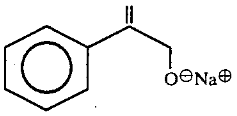

and

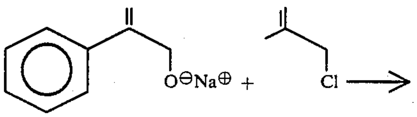

-continued

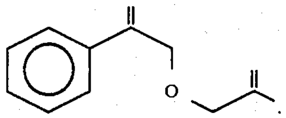

Into a 3 liter reaction flask equipped with stirrer, thermometer, reflux condenser, addition funnel and heating mantle is placed 240 grams of a 50% aqueous solution of sodium hydroxide; 15 grams of ALIQUAT ®336 and 200 ml toluene. The resulting mixture is heated to reflux and over a period of ten minutes, 268 grams of beta-methylene phenylethyl alcohol having the structure:

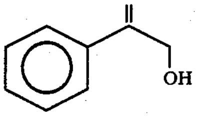

is added followed by addition of 190 grams of 3-chloro-2-methyl-propene over a 25 minute period while refluxing the reaction mass at 104°-110° C. The reaction mass is then continued to be refluxed at a temperature of between 95° and 110° C. for a period of eleven hours. At the end of the eleven hour period, the reaction mass is washed with water. The organic phase is then distilled on a 10" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 60/15 | 104/109 | 0.9/0.0 | 9:1/9:1 | 8.8 |
| 2 | 16 | 110 | 0.9 | 9:1 | 13.4 |
| 3 | 75 | 110 | 0.9 | 9:1 | 20.1 |
| 4 | 73 | 110 | 0.9 | 9:1 | 24.4 |
| 5 | 73 | 110 | 0.9 | 9:1 | 23.3 |
| 6 | 70 | 110 | 0.9 | 9:1 | 24.5 |
| 7 | 70 | 112 | 0.9 | 9:1 | 27.7 |
| 8 | 72 | 114 | 0.9 | 9:1 | 26.9 |
| 9 | 73 | 114 | 0.9 | 9:1 | 21.4 |
| 10 | 73 | 145 | 0.9 | 9:1 | 19.9 |
| 11 | 72 | 120 | 0.8 | 9:1 | 26.3 |
| 12 | 72 | 124 | 0.8 | 9:1 | 14.8 |
| 13 | 72 | 135 | 0.8 | 9:1 | 14.9 |
| 14 | 72 | 147 | 0.8 | 9:1 | 13.6 |
| 15 | 72 | 187 | 0.8 | 9:1 | 10.3 |
| 16 | — | 220 | 0.6 | 9:1 | 8.1 |

Fractions 1-8 are identified as starting material and fractions 9-15 are identified as product having the structure:

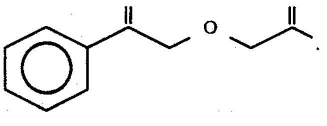

This product has a rose, ozoney and green aroma with fruity topnotes.

FIG. 9 is the GLC profile for the crude reaction product. The peak indicated by reference numeral 92 is the peak for the compound having the structure:

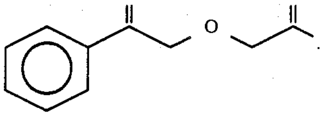

The peak indicated by reference numeral 91 is the peak for the compound having the structure:

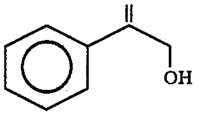

(Conditions: SE-30 column programmed at 180° C. isothermal).

FIG. 10 is the NMR spectrum for the compound having the structure:

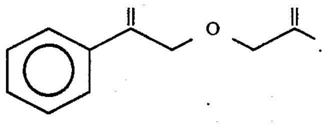

EXAMPLE IV

Preparation of Alpha-Methyl-Phenethyl Methyl Carbonate

Reaction:

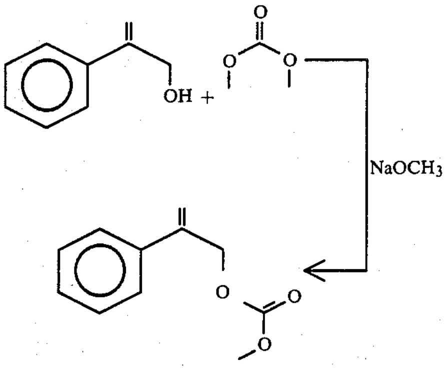

Into a 2 liter reaction flask equipped with stirrer, thermometer, reflux condenser, heating mantle and Bidwell addition funnel is placed 222 grams of dimethyl carbonate and 24 grams of a solution of sodium methoxide in methanol. The resulting mixture is heated to reflux. Over a 30 minute period 268 grams of alpha-methylene phenylethyl alcohol having the structure:

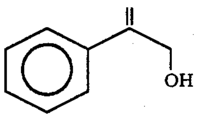

is added over a period of 20 minutes after bringing the mixture to reflux at 72°-76° C. At the end of the addition of the alpha-methylene phenylethyl alcohol the reaction mass is continued to be refluxed at 78° C. for a period of two hours. At the end of the two hour period, the excess methyl alcohol is taken off at 100° C. The reaction mass is then cooled and 200 ml wter is added thereto. The organic phase is then distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 76/80 | 107/110 | 1.0/1.0 | 4:1/4:1 | 27 |
| 2 | 84 | 118 | 1.0 | 4:1 | 27 |
| 3 | 95 | 132 | 1.0 | 4:1 | 22 |
| 4 | 78 | 142 | 0.9 | 8:1 | 26 |
| 5 | 87 | 148 | 0.9 | 8:1 | 25 |
| 6 | 88 | 152 | 0.9 | 8:1 | 15 |
| 7 | 88 | 155 | 0.9 | 8:1 | 11 |
| 8 | 90 | 167 | 1.0 | 8:1 | 15 |
| 9 | 93 | 182 | 1.4 | 8:1 | 8 |
| 10 | 103 | 200 | 2.4 | 8:1 | 8 |
| 11 | 103 | 215 | 3.0 | 8:1 | 10 |
| 12 | 98 | 217 | 2.8 | 8:1 | 7 |
| 13 | 98 | 220 | 2.6 | 8:1 | 7. |

Fractions 1-5 represents starting material. Fractions 6-13 are product having the structure:

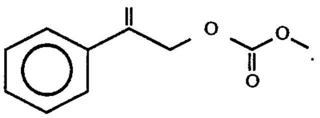

The product having the structure:

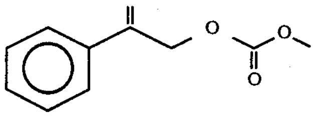

has a rose, lilac and spicy aroma with anisic topnotes.

FIG. 11 is the GLC profile for the crude reaction product. The peak indicated by reference numeral 1112 is the peak for the compound having the structure:

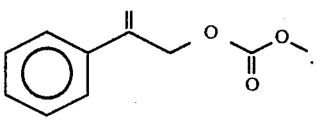

The peak indicated by reference numeral 1110 is the peak for the compound, the starting material, having the structure:

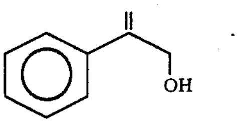

FIG. 12 is the NMR spectrum for the compound having the structure:

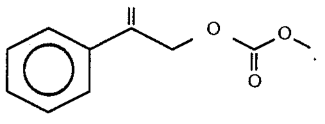

EXAMPLE V

Preparation of Alpha-Methylene Phenethyl Alcohol-1,3,2-Dioxaborinane Derivative

Reactions:

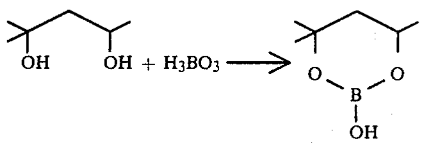

(Example V(A))

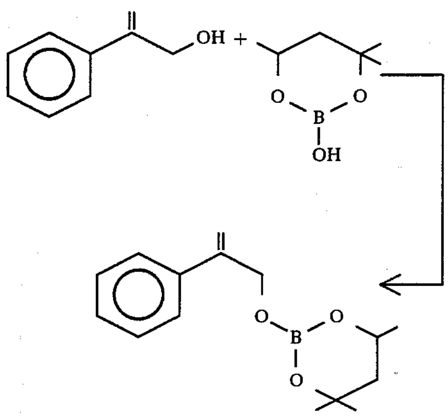

(Example I(B))

EXAMPLE V(A)

Into a 3 liter reaction vessel equipped with stirrer, thermometer, reflux condenser and Dean Start trap is placed 710.0 grams of 2-methyl-2,4-pentanediol; 372.0 grams of boric acid and 500 grams of toluene. With stirring the reaction mass is heated to 87° C. and, by way of the Dean Stark trap water is eliminated and the alcohol having the structure:

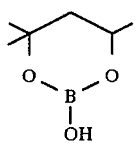

is recovered. The reaction temperature gradually rises to 125° C. as water is eliminated and the total reaction time is 10 hours. The total amount of water evolved is 252.0 grams. When the water of reaction ceases to evolve, the reaction mass is cooled to 70° C. Once all of the water is removed the compound having the structure:

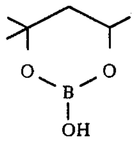

as recovered weighs 1227.0 grams.

EXAMPLE V(B)

Into a 1 liter flask equipped with stirrer, thermometer, reflux condenser and addition funnel (Bidwell apparatus) under a nitrogen blanket is placed 111.0 grams of beta-methylene phenylethyl alcohol having the structure:

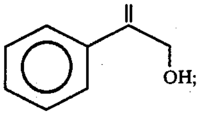

117.0 grams of the compound having the structure:

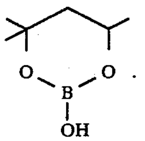

(produced according to Example V(A) and 120.0 cc of cyclohexane.

The water is azeotroped out first.

Over a period of 27 hours while maintaining the reaction mass at 96°–97° C. the reaction mass is refluxed. At the end of the refluxing period, the reaction mass is cooled and distilled on a 4" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 85/102 | 135/163 | 10.0 | 7.0 |
| 2 | 74 | 167 | 11.0 | 16.0 |
| 3 | 152 | 156 | 6.0 | 24.0 |
| 4 | 153 | 157 | 6.4 | 15.0 |
| 5 | 153 | 159 | 6.0 | 23.0 |
| 6 | 154 | 164 | 6.0 | 25.0 |
| 7 | 153 | 164 | 6.0 | 18.0 |
| 8 | 154 | 187 | 6.0 | 16.0 |
| 9 | 154 | 200 | 2.0 | 3.0. |

The resulting product having the structure:

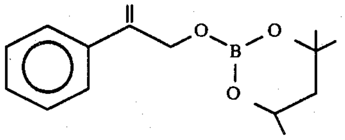

has a rose, cinnamon and carnation aroma with spicy, clove, lilac and piney topnotes.

FIG. 13 is the GLC profile for the crude reaction product (Conditions: SE-30 column programmed at 100°–220° C. at 16° C. per minute).

FIG. 14 is the GLC profile for bulked distillation fractions 4–8 for the foregoing distillation (Conditions: SE-30 column programmed at 100°–220° C. at 16° C. per minute).

FIG. 15 is the NMR spectrum for the reaction product having the structure:

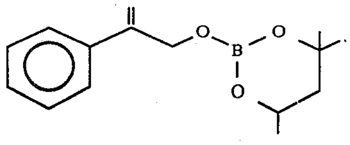

FIG. 16 is the infra-red spectrum for the reaction product having the structure:

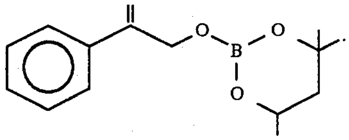

EXAMPLE VI

Perfume Formulation

The following floral/vetiver perfume formulation is prepared:

| | Parts by Weight | | |
|---|---|---|---|
| Ingredients | VI(A) | VI(B) | VI(C) |
| Vetivone | 25.0 | 25.0 | 25.0 |
| Compound having the structure: 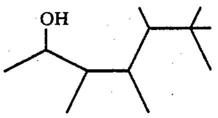 produced according to Example III of U.S. Letters Pat. No. 4,391,999, bulked fractions 12-15. | 25.0 | 25.0 | 25.0 |
| Vetiverol | 5.0 | 5.0 | 5.0 |
| Musk Ketone | 8.0 | 8.0 | 8.0 |
| Styrax essence | 12.5 | 12.5 | 12.5 |
| Geraniol | 32.4 | 32.4 | 32.4 |
| Phenylethyl alcohol | 12.8 | 12.8 | 12.8 |
| Compound having the structure: 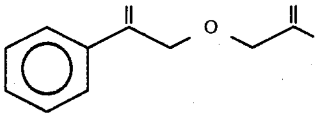 prepared according to Example III. | 15.0 | 0 | 0 |
| Compound having the structure: 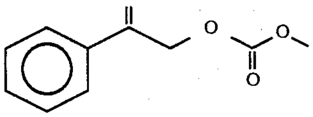 produced according to Example IV. | 0 | 15.0 | 0 |
| Compound having the structure: | 0 | 0 | 15.0 |

-continued

| Ingredients | Parts by Weight VI(A) | VI(B) | VI(C) |
|---|---|---|---|
| 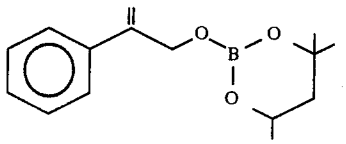 prepared according to Example V. | | | |

The perfume composition of Example VI(A) has a floral and vetiver aroma with rose, ozoney and green undertones and a fruity topnote.

The perfume composition prepared according to Example VI(B) has a floral and vetiver aroma with rose, lilac and spicy undertones and an anisic topnote.

The perfume composition of Example VI(C) has a vetiver and floral aroma with rose, cinnamon and carnation undertones and spicy, clove, lilac and piney topnotes.

EXAMPLE VII

Perfumed Liquid Detergent

Concentrated liquid detergents with aromas as described in Table I below (which detergents are produced from the lysine salt of n-dodecyl benzene sulfonic acid as more specifically described in U.S. Pat. No. 3,948,818 issued on Apr. 6, 1976) are prepared containing one of the substances set forth in Table I below. They are prepared by adding and homogeneously mixing the appropriate quantity of substance as indicated in Table I below. The detergents all possess aroma profiles as set forth in Table I below, the intensity increasing with greater concentrations of the composition of matter as set forth in Table I below:

TABLE I

| Aroma Ingredient | Aroma Profile |
|---|---|
| The compound having 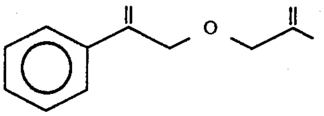 produced according to Example III. | A rose, ozoney and green aroma profile with fruity topnotes. |
| Compound having the structure: 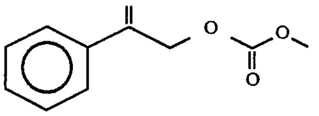 produced according to Example IV. | A rose, lilac and spicy aroma profile with anisic topnotes. |
| Compound having the structure: 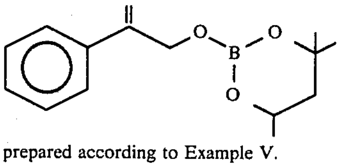 prepared according to Example V. | A rose, cinnamon and carnation aroma with spicy, clove, lilac and piney topnotes. |
| Perfume composition of Example VI(A). | A floral and vetiver aroma with rose, ozoney and green undertones and a fruity topnote. |
| Perfume composition of Example VI(B). | A floral and vetiver aroma with rose, lilac and spicy undertones and an anisic topnote. |
| Perfume composition of Example VI(C). | A vetiver and floral aroma with rose, cinnamon and carnation undertones and spicy, clove, lilac and piney topnotes. |

EXAMPLE VIII

Preparation of a Cologne and Handkerchief Perfume

Aroma imparting and augmenting ingredients as defined according to Table I of Example VII are incorporated into colognes at concentrations of 1.5%, 2.0%, 2.5%, 3.0%, 4.0% and 5.0% in 75%, 80% 90% and 95% solutions of aqueous ethanol; and into handkerchief perfumes at concentrations of 15%, 20%, 25% and 30% (in 80%, 85% and 95% aqueous ethanol solutions). The use of the compositions of matter as set forth in Table I of Example VII affords distinct and definitive aroma profiles as set forth in Table I of Example VII to the handkerchief perfumes and the colognes.

EXAMPLE IX

Preparation of a Soap Composition

One hundred grams of soap chips (IVORY ® manufactured by the Proctor & Gamble Company of Cincinnati, Ohio), are melted and intimately admixed with one of the aroma materials as set forth in Table I of Example VII, supra, the amount of composition of matter of Table I of Example VII being one gram of each composition of matter. The conditions of mixing are: 180° C., 3 hours, 12 atmospheres pressure. At the end of the mixing cycle, while the soap is still under 12 atmospheres pressure, the mixture of soap and perfume of ingredient is cooled to room temperature. At this temperature, the resulting mixture is in a solid state. The resulting soap block is then cut up into soap cakes. Each of the soap cakes manifests an excellent aroma as set forth in Table I of Example VII. None of the soap samples show any discoloration even after two weeks in the oven at 90° F.

EXAMPLE X

Preparation of a Detergent Composition

A total of 100 grams of a detergent powder (nonionic detergent powder containing a proteolytic enzyme prepared according to Example I of Canadian Pat. No. 985,190 issued on Mar. 9, 1976) is mixed with 0.15 grams of one of the compositions of matter as set forth in Table I of Example VII until a substantially homogeneous composition is obtained. Each of the compositions has excellent aroma profiles as set forth in Table I of Example VII.

EXAMPLE XI

Perfumed Liquid Detergents

Concentrated liquid detergents with rich, pleasant aromas as set forth in Table I of Example VII are prepared containing 0.10%, 0.15% and 0.20% of each of the compositions of matter set forth in Table I of Example VII. They are prepared by adding and homogeneously admixing the appropriate quantity of composition of matter of Table I of Example VII in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table I of Example VII, the intensity increasing with greater concentrations of composition of matter of Table I of Example VII.

What is claimed is:

1. The beta-alkylidene phenethyl alcohol esters and ethers defined according to the structure:

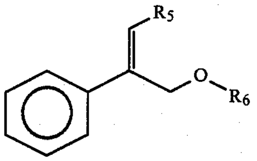

wherein $R_5$ represents hydrogen or methyl; wherein $R_6$ represents one of the moieties:

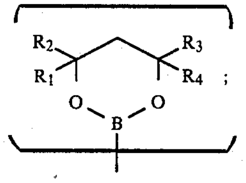

;

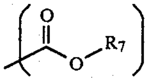

;

or

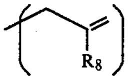

;

wherein $R_1$, $R_2$, $R_3$ and $R_4$ each represents the same or different hydrogen or methyl; wherein $R_7$ represents methyl or ethyl; and wherein $R_8$ represents hydrogen or methyl.

2. The beta-alkylidene phenethyl alcohol esters and ethers of claim 1 defined according to the structure:

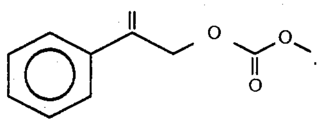

3. The beta-alkylidene phenethyl alcohol esters and ethers of claim 1 having the structure:

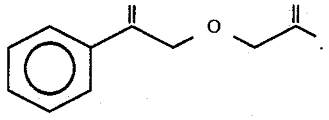

4. The beta-alkylidene phenethyl alcohol esters and ethers of claim 1 having the structure:

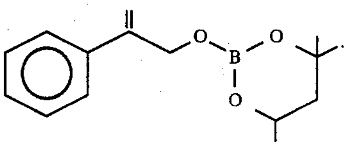

5. The process for augmenting or enhancing the aroma of a consumable material selected from the group consisting of perfume compositions, perfumed articles and colognes comprising the step of intimately admixing with said consumable material, an aroma augmenting or enhancing quantity of at least one compound defined according to claim 1.

6. A process for augmenting or enhancing the aroma of a perfume composition, cologne, perfumed polymer or perfumed article on contact with water or water vapor comprising the step of intimately admixing said perfume composition, cologne, perfumed article or perfumed polymer with at least one 1,3,2-dioxaborinane derivative defined according to claim 4 and then contacting said perfume composition, perfumed article, perfumed polymer or cologne with water or water vapor.

7. A perfumed polymer consisting essentially of a microporous polymer containing interconnected voids and filling said interconnected voids a perfumery composition containing a substantial quantity of at least one 1,3,2-dioxaborinane derivative defined according to claim 4.

* * * * *